(12) United States Patent
Honaryar et al.

(10) Patent No.: US 8,876,694 B2
(45) Date of Patent: Nov. 4, 2014

(54) TUBE CONNECTOR WITH A GUIDING TIP

(75) Inventors: Babak Honaryar, Orinda, CA (US);
Sean Snow, Carpinteria, CA (US);
Marcos Borrell, Goleta, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 123 days.

(21) Appl. No.: 13/313,998

(22) Filed: Dec. 7, 2011

(65) Prior Publication Data
US 2013/0150664 A1 Jun. 13, 2013

(51) Int. Cl.
| A61F 2/00 | (2006.01) |
| A61F 13/00 | (2006.01) |
| A61N 2/00 | (2006.01) |
| A61F 5/02 | (2006.01) |

(52) U.S. Cl.
CPC ............... *A61N 2/008* (2013.01); *A61F 5/028* (2013.01)
USPC .................... 600/37; 606/151; 604/9; 602/19

(58) Field of Classification Search
USPC .................... 600/37; 606/151; 604/9; 602/19
See application file for complete search history.

(56) References Cited

U.S. PATENT DOCUMENTS

| 1,174,814 A | 3/1916 | Brennan et al. |
| 2,936,980 A | 5/1930 | Rapata |
| 1,830,947 A | 11/1931 | Klingel |
| 1,999,683 A | 4/1935 | Borresen |
| 2,163,048 A | 6/1939 | McKee |
| 2,339,138 A | 1/1944 | Black |
| 2,405,667 A | 8/1946 | Ottesen |
| 2,438,231 A | 3/1948 | Schultz et al. |
| 2,635,907 A | 4/1953 | Heimbuch |
| 2,714,469 A | 8/1955 | Carlson |
| 3,059,645 A | 10/1962 | Hasbrouck et al. |
| 3,189,961 A | 6/1965 | Heller |
| 3,667,081 A | 6/1972 | Burger |
| 3,840,018 A | 10/1974 | Heifetz |
| 3,955,834 A | 5/1976 | Ahlrot |

(Continued)

FOREIGN PATENT DOCUMENTS

| CA | 949965 | 6/1974 |
| CN | 1250382 | 4/2000 |

(Continued)

OTHER PUBLICATIONS

"Innovative medical devices and implants"; LGSP medical futures, p. 5.

(Continued)

*Primary Examiner* — Christine Matthews
*Assistant Examiner* — Sunita Reddy
(74) *Attorney, Agent, or Firm* — Gordon & Jacobson, PC

(57) ABSTRACT

Generally described herein are apparatus, systems and methods related to utilizing a guiding tip to connect two open ends of respective tubes of a gastric banding system. More particularly, one of these tubes may include a barbed element at or near the point of connection which makes it difficult to connect the two tubes as the barbed element may be larger than an opening to receive the barbed element. The guiding tip provides a solution to this problem by acting as an interface between the barbed element and the receiving tube. In this manner, the sealing functionality of the barbed element may be retained while improving the ease of inserting the barbed element into the receiving tube.

20 Claims, 9 Drawing Sheets

(56) References Cited

U.S. PATENT DOCUMENTS

| | | | |
|---|---|---|---|
| 4,053,176 A | 10/1977 | Hilbush |
| 4,118,805 A | 10/1978 | Reimels |
| 4,133,315 A | 1/1979 | Berman et al. |
| 4,157,713 A | 6/1979 | Clarey |
| 4,176,412 A | 12/1979 | Peterson |
| 4,236,521 A | 12/1980 | Lauterjung |
| 4,271,827 A | 6/1981 | Angelchick |
| 4,299,012 A | 11/1981 | Oetiker |
| 4,340,083 A | 7/1982 | Cummins |
| 4,399,809 A | 8/1983 | Baro et al. |
| 4,406,656 A | 9/1983 | Hattler et al. |
| 4,408,597 A | 10/1983 | Tenney, Jr. et al. |
| 4,417,567 A | 11/1983 | Trick |
| 4,424,208 A | 1/1984 | Wallace et al. |
| 4,442,153 A | 4/1984 | Meltsch |
| 4,450,375 A | 5/1984 | Siegal |
| 4,485,805 A | 12/1984 | Foster, Jr. |
| 4,492,004 A | 1/1985 | Oetiker |
| 4,551,862 A | 11/1985 | Haber |
| 4,558,699 A | 12/1985 | Bashour |
| 4,559,699 A | 12/1985 | Owen et al. |
| 4,582,640 A | 4/1986 | Smestad et al. |
| 4,582,865 A | 4/1986 | Balazs et al. |
| 4,592,339 A | 6/1986 | Kuzmak et al. |
| 4,592,355 A | 6/1986 | Antebi |
| 4,601,713 A | 7/1986 | Fuqua |
| 4,667,672 A | 5/1987 | Romanowski |
| 4,671,351 A | 6/1987 | Rappe |
| 4,693,695 A | 9/1987 | Cheng |
| 4,694,827 A | 9/1987 | Weiner et al. |
| 4,696,288 A | 9/1987 | Kuzmak et al. |
| 4,708,140 A | 11/1987 | Baron |
| 4,716,154 A | 12/1987 | Malson et al. |
| 4,753,086 A | 6/1988 | Schmidt |
| 4,760,837 A | 8/1988 | Petit |
| 4,803,075 A | 2/1989 | Wallace et al. |
| 4,881,939 A | 11/1989 | Newman |
| 4,883,467 A | 11/1989 | Franetzki et al. |
| 4,886,787 A | 12/1989 | De Belder et al. |
| 4,896,787 A | 1/1990 | Delamour et al. |
| 4,915,690 A | 4/1990 | Cone et al. |
| 4,925,446 A | 5/1990 | Garay et al. |
| 4,944,487 A | 7/1990 | Holtermann |
| 4,944,659 A | 7/1990 | Labbe et al. |
| 4,958,791 A | 9/1990 | Nakamura |
| 4,969,899 A | 11/1990 | Cox, Jr. |
| 4,994,019 A | 2/1991 | Fernandez et al. |
| 5,045,060 A | 9/1991 | Melsky et al. |
| 5,074,868 A | 12/1991 | Kuzmak |
| 5,084,061 A | 1/1992 | Gau et al. |
| 5,091,171 A | 2/1992 | Yu et al. |
| 5,116,652 A | 5/1992 | Alzner |
| 5,120,313 A | 6/1992 | Elftman |
| 5,143,724 A | 9/1992 | Leshchiner et al. |
| 5,152,770 A | 10/1992 | Bengmark et al. |
| 5,160,338 A | 11/1992 | Vincent |
| 5,188,609 A | 2/1993 | Bayless et al. |
| 5,224,494 A | 7/1993 | Enhorning |
| 5,226,429 A | 7/1993 | Kuzmak |
| 5,246,456 A | 9/1993 | Wilkinson |
| 5,246,698 A | 9/1993 | Leshchiner et al. |
| 5,259,399 A | 11/1993 | Brown |
| 5,326,349 A | 7/1994 | Baraff |
| 5,343,894 A | 9/1994 | Frisch et al. |
| 5,356,883 A | 10/1994 | Kuo et al. |
| 5,360,445 A | 11/1994 | Goldowsky |
| 5,391,156 A | 2/1995 | Hildwein et al. |
| 5,399,351 A | 3/1995 | Leshchiner et al. |
| 5,449,363 A | 9/1995 | Brust et al. |
| 5,449,368 A | 9/1995 | Kuzmak |
| 5,458,568 A | 10/1995 | Racchini et al. |
| 5,509,888 A | 4/1996 | Miller |
| 5,531,716 A | 7/1996 | Luzio et al. |
| 5,535,752 A | 7/1996 | Halperin et al. |
| 5,554,113 A | 9/1996 | Novak et al. |
| 5,562,714 A | 10/1996 | Grevious |
| 5,601,604 A | 2/1997 | Vincent |
| 5,607,418 A | 3/1997 | Arzbaecher |
| 5,633,001 A | 5/1997 | Agerup |
| 5,653,718 A | 8/1997 | Yoon |
| 5,658,298 A | 8/1997 | Vincent et al. |
| 5,676,162 A | 10/1997 | Larson, Jr. et al. |
| 5,695,504 A | 12/1997 | Gifford, III et al. |
| 5,704,893 A | 1/1998 | Timm |
| 5,713,911 A | 2/1998 | Racenet et al. |
| 5,733,257 A | 3/1998 | Sternby |
| 5,748,200 A | 5/1998 | Funahashi |
| 5,766,232 A | 6/1998 | Grevious et al. |
| 5,769,877 A | 6/1998 | Barreras, Sr. |
| 5,785,295 A | 7/1998 | Tsai |
| 5,807,311 A | 9/1998 | Palestrant |
| 5,817,113 A | 10/1998 | Gifford, III et al. |
| 5,827,529 A | 10/1998 | Ono et al. |
| 5,833,698 A | 11/1998 | Hinchliffe et al. |
| 5,861,014 A | 1/1999 | Familoni |
| RE36,176 E | 3/1999 | Kuzmak |
| 5,886,042 A | 3/1999 | Yu et al. |
| 5,904,697 A | 5/1999 | Gifford, III et al. |
| 5,910,149 A | 6/1999 | Kuzmak |
| 5,928,195 A | 7/1999 | Malamud et al. |
| 5,938,669 A | 8/1999 | Klaiber et al. |
| 5,944,696 A | 8/1999 | Bayless et al. |
| 5,944,751 A | 8/1999 | Laub |
| 5,993,473 A | 11/1999 | Chan et al. |
| 6,013,679 A | 1/2000 | Kuo et al. |
| 6,024,340 A | 2/2000 | Lazarus et al. |
| 6,024,704 A | 2/2000 | Meador et al. |
| 6,048,309 A | 4/2000 | Flom et al. |
| 6,067,991 A | 5/2000 | Forsell |
| 6,074,341 A | 6/2000 | Anderson et al. |
| 6,074,378 A | 6/2000 | Mouri et al. |
| 6,083,249 A | 7/2000 | Familoni |
| 6,090,131 A | 7/2000 | Daley |
| 6,102,678 A | 8/2000 | Peclat |
| 6,102,922 A | 8/2000 | Jakobsson et al. |
| 6,171,321 B1 | 1/2001 | Gifford, III et al. |
| 6,193,734 B1 | 2/2001 | Bolduc et al. |
| 6,203,523 B1 | 3/2001 | Haller et al. |
| 6,210,345 B1 | 4/2001 | Van Brunt |
| 6,210,347 B1 | 4/2001 | Forsell |
| 6,221,024 B1 | 4/2001 | Miesel |
| 6,224,857 B1 | 5/2001 | Romeo et al. |
| 6,306,088 B1 | 10/2001 | Krausman et al. |
| 6,327,503 B1 | 12/2001 | Familoni |
| 6,371,965 B2 | 4/2002 | Gifford, III et al. |
| 6,372,494 B1 | 4/2002 | Naughton et al. |
| 6,383,218 B1 | 5/2002 | Sourdile et al. |
| 6,383,219 B1 | 5/2002 | Telandro et al. |
| 6,387,105 B1 | 5/2002 | Gifford, III et al. |
| 6,417,750 B1 | 7/2002 | Sohn |
| 6,418,934 B1 | 7/2002 | Chin |
| 6,419,696 B1 | 7/2002 | Ortiz et al. |
| 6,432,040 B1 | 8/2002 | Meah |
| 6,439,539 B1 | 8/2002 | Powell |
| 6,443,957 B1 | 9/2002 | Addis |
| 6,443,965 B1 | 9/2002 | Gifford, III et al. |
| 6,450,173 B1 | 9/2002 | Forsell |
| 6,450,946 B1 | 9/2002 | Forsell |
| 6,450,987 B1 | 9/2002 | Kramer |
| 6,451,034 B1 | 9/2002 | Gifford, III et al. |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyos Garza |
| 6,457,801 B1 | 10/2002 | Fish et al. |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,474,584 B2 | 11/2002 | Ekich |
| 6,475,136 B1 | 11/2002 | Forsell |
| 6,485,496 B1 | 11/2002 | Suyker et al. |

(56) References Cited

U.S. PATENT DOCUMENTS

| | | |
|---|---|---|
| 6,491,704 B2 | 12/2002 | Gifford, III et al. |
| 6,491,705 B2 | 12/2002 | Gifford, III et al. |
| 6,511,490 B2 | 1/2003 | Robert |
| 6,517,556 B1 | 2/2003 | Monassevitch |
| 6,527,701 B1 | 3/2003 | Sayet et al. |
| 6,547,801 B1 | 4/2003 | Dargent et al. |
| 6,565,582 B2 | 5/2003 | Gifford, III et al. |
| 6,579,301 B1 | 6/2003 | Bales et al. |
| 6,601,604 B1 | 8/2003 | Cooper |
| 6,615,084 B1 | 9/2003 | Cigaina |
| 6,627,620 B1 | 9/2003 | Nielsen |
| 6,630,486 B1 | 10/2003 | Royer |
| 6,632,239 B2 | 10/2003 | Snyder et al. |
| 6,646,628 B2 | 11/2003 | Shirochi et al. |
| 6,676,674 B1 | 1/2004 | Dudai |
| 6,685,668 B1 | 2/2004 | Cho et al. |
| 6,685,963 B1 | 2/2004 | Taupin et al. |
| 6,691,047 B1 | 2/2004 | Fredericks |
| 6,715,731 B1 | 4/2004 | Post et al. |
| 6,729,600 B2 | 5/2004 | Mattes et al. |
| 6,754,527 B2 | 6/2004 | Stroebel et al. |
| 6,767,924 B2 | 7/2004 | Yu et al. |
| 6,811,136 B2 | 11/2004 | Eberhardt et al. |
| 6,820,651 B2 | 11/2004 | Seuret et al. |
| 6,834,201 B2 | 12/2004 | Gillies et al. |
| 6,871,090 B1 | 3/2005 | He et al. |
| 6,889,086 B2 | 5/2005 | Mass et al. |
| 6,916,326 B2 | 7/2005 | Benchetrit |
| 6,921,819 B2 | 7/2005 | Piron et al. |
| 6,924,273 B2 | 8/2005 | Pierce |
| 6,940,467 B2 | 9/2005 | Fisher et al. |
| 6,966,875 B1 | 11/2005 | Longobardi |
| 7,017,583 B2 | 3/2006 | Forsell |
| 7,021,147 B1 | 4/2006 | Subramanian et al. |
| 7,037,344 B2 | 5/2006 | Kagan et al. |
| 7,040,349 B2 | 5/2006 | Moler et al. |
| 7,054,690 B2 | 5/2006 | Imran |
| 7,058,434 B2 | 6/2006 | Wang et al. |
| 7,060,080 B2 | 6/2006 | Bachmann |
| 7,066,486 B2 | 6/2006 | Birk |
| 7,118,526 B2 | 10/2006 | Egle |
| 7,119,062 B1 | 10/2006 | Alvis et al. |
| 7,128,750 B1 | 10/2006 | Stergiopulos |
| 7,144,400 B2 | 12/2006 | Byrum et al. |
| 7,172,607 B2 | 2/2007 | Hofle et al. |
| 7,177,693 B2 | 2/2007 | Starkebsum |
| 7,191,007 B2 | 3/2007 | Desai et al. |
| 7,204,821 B1 | 4/2007 | Clare et al. |
| 7,223,239 B2 | 5/2007 | Schulze et al. |
| 7,238,191 B2 | 7/2007 | Bachmann |
| 7,240,607 B2 | 7/2007 | Fish |
| 7,255,675 B2 | 8/2007 | Gertner et al. |
| 7,263,405 B2 | 8/2007 | Boveja et al. |
| 7,282,023 B2 | 10/2007 | Frering |
| 7,288,064 B2 | 10/2007 | Boustani et al. |
| 7,297,103 B2 | 11/2007 | Jarsaillon et al. |
| 7,299,082 B2 | 11/2007 | Feldman et al. |
| 7,310,557 B2 | 12/2007 | Maschino et al. |
| 7,311,716 B2 | 12/2007 | Byrun |
| 7,311,717 B2 | 12/2007 | Egle |
| 7,314,443 B2 | 1/2008 | Jordan et al. |
| 7,314,636 B2 | 1/2008 | Caseres et al. |
| 7,338,433 B2 | 3/2008 | Coe |
| 7,340,306 B2 | 3/2008 | Barrett et al. |
| 7,351,198 B2 | 4/2008 | Byrum et al. |
| 7,351,240 B2 | 4/2008 | Hassler, Jr. et al. |
| 7,364,542 B2 | 4/2008 | Jambor et al. |
| 7,367,340 B2 | 5/2008 | Nelson et al. |
| 7,367,937 B2 | 5/2008 | Jambor et al. |
| 7,374,565 B2 | 5/2008 | Hassler, Jr. et al. |
| 7,390,294 B2 | 6/2008 | Hassler, Jr. |
| 7,396,353 B2 | 7/2008 | Lorenzen et al. |
| 7,416,528 B2 | 8/2008 | Crawford et al. |
| 7,457,668 B2 | 11/2008 | Cancel et al. |
| 7,481,763 B2 | 1/2009 | Hassler, Jr. et al. |
| 7,500,944 B2 | 3/2009 | Byrum et al. |
| 7,502,649 B2 | 3/2009 | Ben-Haim et al. |
| 7,530,943 B2 | 5/2009 | Lechner |
| 7,594,885 B2 | 9/2009 | Byrum |
| 7,599,743 B2 | 10/2009 | Hassler, Jr. et al. |
| 7,599,744 B2 | 10/2009 | Giordano et al. |
| 7,601,162 B2 | 10/2009 | Hassler, Jr. et al. |
| 7,615,001 B2 | 11/2009 | Jambor et al. |
| 7,618,365 B2 | 11/2009 | Jambor et al. |
| 7,658,196 B2 | 2/2010 | Ferreri et al. |
| 7,670,279 B2 | 3/2010 | Gertner |
| 7,699,770 B2 | 4/2010 | Hassler, Jr. et al. |
| 7,712,470 B2 | 5/2010 | Gertner |
| 7,727,141 B2 | 6/2010 | Hassler, Jr. et al. |
| 7,741,476 B2 | 6/2010 | Lebreton |
| 7,758,493 B2 | 7/2010 | Gingras |
| 7,763,039 B2 | 7/2010 | Ortiz et al. |
| 7,766,815 B2 | 8/2010 | Ortiz |
| 7,771,439 B2 | 8/2010 | Griffiths |
| 7,775,215 B2 | 8/2010 | Hassler, Jr. et al. |
| 7,775,966 B2 | 8/2010 | Dlugos et al. |
| 7,775,967 B2 | 8/2010 | Gertner |
| 7,794,386 B2 | 9/2010 | Brooks |
| 7,811,298 B2 | 10/2010 | Birk |
| 7,824,422 B2 | 11/2010 | Benchetrit |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos, Jr. et al. |
| 7,862,502 B2 | 1/2011 | Pool et al. |
| 7,879,068 B2 | 2/2011 | Dlugos et al. |
| 7,951,067 B2 | 5/2011 | Byrum et al. |
| 2001/0011543 A1 | 8/2001 | Forsell |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0139208 A1 | 10/2002 | Yatskov |
| 2002/0183765 A1 | 12/2002 | Adams |
| 2002/0193679 A1 | 12/2002 | Malave et al. |
| 2002/0198548 A1 | 12/2002 | Robert |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0060873 A1 | 3/2003 | Gertner et al. |
| 2003/0066536 A1 | 4/2003 | Forsell |
| 2003/0073880 A1 | 4/2003 | Polsky et al. |
| 2003/0093157 A1 | 5/2003 | Casares et al. |
| 2003/0100910 A1 | 5/2003 | Gifford, III et al. |
| 2003/0120288 A1 | 6/2003 | Benchetrit |
| 2003/0148995 A1 | 8/2003 | Piron et al. |
| 2003/0158564 A1 | 8/2003 | Benchetrit |
| 2003/0158569 A1 | 8/2003 | Wazne |
| 2003/0181890 A1 | 9/2003 | Schulze et al. |
| 2003/0181917 A1 | 9/2003 | Gertner |
| 2003/0191433 A1 | 10/2003 | Prentiss |
| 2003/0208212 A1 | 11/2003 | Cigaina |
| 2004/0000843 A1 | 1/2004 | East |
| 2004/0044332 A1 | 3/2004 | Stergiopulos |
| 2004/0049209 A1 | 3/2004 | Benchetrit |
| 2004/0059393 A1 | 3/2004 | Policker et al. |
| 2004/0068847 A1 | 4/2004 | Belisle et al. |
| 2004/0106899 A1 | 6/2004 | McMichael et al. |
| 2004/0133219 A1 | 7/2004 | Forsell |
| 2004/0147816 A1 | 7/2004 | Policker et al. |
| 2004/0148034 A1 | 7/2004 | Kagan et al. |
| 2004/0153106 A1 | 8/2004 | Dudai |
| 2004/0162595 A1 | 8/2004 | Foley |
| 2004/0215159 A1 | 10/2004 | Forsell |
| 2004/0230137 A1 | 11/2004 | Mouton |
| 2004/0254536 A1 | 12/2004 | Conlon et al. |
| 2004/0254537 A1 | 12/2004 | Conlon et al. |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |

(56) References Cited

U.S. PATENT DOCUMENTS

| | | |
|---|---|---|
| 2005/0002984 A1 | 1/2005 | Byrum et al. |
| 2005/0038484 A1 | 2/2005 | Knudson et al. |
| 2005/0038498 A1 | 2/2005 | Dubrow et al. |
| 2005/0055039 A1 | 3/2005 | Burnett et al. |
| 2005/0070934 A1 | 3/2005 | Tanaka et al. |
| 2005/0070937 A1 | 3/2005 | Jambor et al. |
| 2005/0100779 A1 | 5/2005 | Gertner |
| 2005/0104457 A1 | 5/2005 | Jordan et al. |
| 2005/0082793 A1 | 6/2005 | Birk |
| 2005/0119672 A1 | 6/2005 | Benchetrit |
| 2005/0119674 A1 | 6/2005 | Gingras |
| 2005/0131383 A1 | 6/2005 | Chen et al. |
| 2005/0131485 A1 | 6/2005 | Krundson et al. |
| 2005/0136122 A1 | 6/2005 | Sadozai et al. |
| 2005/0142152 A1 | 6/2005 | Leshchiner et al. |
| 2005/0143765 A1 | 6/2005 | Bachmann et al. |
| 2005/0143766 A1 | 6/2005 | Bachmann et al. |
| 2005/0154274 A1 | 7/2005 | Jarsaillon et al. |
| 2005/0171568 A1 | 8/2005 | Duffy |
| 2005/0183730 A1 | 8/2005 | Byrum |
| 2005/0192531 A1 | 9/2005 | Birk |
| 2005/0192601 A1 | 9/2005 | Demarais |
| 2005/0192614 A1 | 9/2005 | Binmoeller |
| 2005/0192629 A1 | 9/2005 | Saadat et al. |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan et al. |
| 2005/0244288 A1 | 11/2005 | O'Neill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler, Jr. |
| 2005/0267500 A1 | 12/2005 | Hassler, Jr. |
| 2005/0267533 A1 | 12/2005 | Gertner |
| 2005/0271729 A1 | 12/2005 | Wang |
| 2005/0277899 A1 | 12/2005 | Conlon et al. |
| 2005/0283041 A1 | 12/2005 | Egle |
| 2005/0288739 A1 | 12/2005 | Hassler, Jr. et al. |
| 2005/0288740 A1 | 12/2005 | Hassler, Jr. et al. |
| 2006/0015138 A1 | 1/2006 | Gertner |
| 2006/0020298 A1 | 1/2006 | Camilleri et al. |
| 2006/0041183 A1 | 2/2006 | Massen et al. |
| 2006/0074439 A1 | 4/2006 | Garner et al. |
| 2006/0074473 A1 | 4/2006 | Gertner |
| 2006/0089571 A1 | 4/2006 | Gertner |
| 2006/0122147 A1 | 6/2006 | Wohlrab |
| 2006/0142700 A1 | 6/2006 | Sobelman et al. |
| 2006/0142790 A1 | 6/2006 | Gertner |
| 2006/0161139 A1 | 7/2006 | Levine et al. |
| 2006/0161186 A1 | 7/2006 | Hassler, Jr. et al. |
| 2006/0167531 A1 | 7/2006 | Gertner et al. |
| 2006/0173238 A1 | 8/2006 | Starkebaum |
| 2006/0173424 A1 | 8/2006 | Conlon |
| 2006/0183967 A1 | 8/2006 | Lechner |
| 2006/0189887 A1 | 8/2006 | Hassler, Jr. et al. |
| 2006/0189888 A1 | 8/2006 | Hassler, Jr. et al. |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0212051 A1 | 9/2006 | Snyder et al. |
| 2006/0212053 A1 | 9/2006 | Gertner |
| 2006/0235448 A1* | 10/2006 | Roslin et al. ............... 606/157 |
| 2006/0246137 A1 | 11/2006 | Hermitte et al. |
| 2006/0247721 A1 | 11/2006 | Maschino et al. |
| 2006/0247722 A1 | 11/2006 | Maschino et al. |
| 2006/0247724 A1 | 11/2006 | Gerber et al. |
| 2006/0252982 A1 | 11/2006 | Hassler, Jr. |
| 2006/0252983 A1 | 11/2006 | Lembo et al. |
| 2006/0257488 A1 | 11/2006 | Hubbard |
| 2006/0264699 A1 | 11/2006 | Gertner |
| 2006/0276812 A1 | 12/2006 | Hill et al. |
| 2006/0293627 A1 | 12/2006 | Byrum et al. |
| 2007/0015954 A1 | 1/2007 | Dlugos |
| 2007/0015955 A1 | 1/2007 | Tsonton |
| 2007/0015956 A1 | 1/2007 | Crawford et al. |
| 2007/0016231 A1 | 1/2007 | Jambor et al. |
| 2007/0016262 A1 | 1/2007 | Gross et al. |
| 2007/0027356 A1 | 2/2007 | Ortiz |
| 2007/0027358 A1 | 2/2007 | Gertner et al. |
| 2007/0044655 A1 | 3/2007 | Fish |
| 2007/0077292 A1 | 4/2007 | Pinsky |
| 2007/0078476 A1 | 4/2007 | Hull, Sr. et al. |
| 2007/0125826 A1 | 6/2007 | Shelton |
| 2007/0156013 A1 | 7/2007 | Birk |
| 2007/0167672 A1 | 7/2007 | Dlugos et al. |
| 2007/0167982 A1 | 7/2007 | Gertner et al. |
| 2007/0173685 A1 | 7/2007 | Jambor et al. |
| 2007/0173888 A1 | 7/2007 | Gertner et al. |
| 2007/0179335 A1 | 8/2007 | Gertner et al. |
| 2007/0185373 A1 | 8/2007 | Tsonton |
| 2007/0185462 A1 | 8/2007 | Byrum |
| 2007/0213836 A1 | 9/2007 | Paganon |
| 2007/0218083 A1 | 9/2007 | Brooks |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann et al. |
| 2007/0250086 A1 | 10/2007 | Wiley et al. |
| 2007/0255335 A1 | 11/2007 | Herbert et al. |
| 2007/0255336 A1 | 11/2007 | Herbert et al. |
| 2007/0265598 A1 | 11/2007 | Karasik |
| 2007/0265645 A1 | 11/2007 | Birk et al. |
| 2007/0265646 A1 | 11/2007 | McCoy et al. |
| 2007/0293716 A1 | 12/2007 | Baker et al. |
| 2007/0298005 A1 | 12/2007 | Thibault |
| 2008/0009680 A1 | 1/2008 | Hassler, Jr. |
| 2008/0015406 A1 | 1/2008 | Dlugos et al. |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097496 A1 | 4/2008 | Chang et al. |
| 2008/0108862 A1 | 5/2008 | Jordan et al. |
| 2008/0147002 A1 | 6/2008 | Gertner |
| 2008/0161717 A1 | 7/2008 | Gertner |
| 2008/0161875 A1 | 7/2008 | Stone |
| 2008/0167647 A1 | 7/2008 | Gertner |
| 2008/0167648 A1 | 7/2008 | Gertner |
| 2008/0172072 A1 | 7/2008 | Pool et al. |
| 2008/0188766 A1 | 8/2008 | Gertner |
| 2008/0195092 A1 | 8/2008 | Kim et al. |
| 2008/0208240 A1 | 8/2008 | Paz |
| 2008/0221598 A1 | 9/2008 | Dlugos et al. |
| 2008/0243071 A1 | 10/2008 | Quijano et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1* | 11/2008 | Tsonton et al. ............... 606/151 |
| 2008/0287974 A1 | 11/2008 | Widenhouse et al. |
| 2008/0287976 A1 | 11/2008 | Weaner et al. |
| 2008/0300618 A1 | 12/2008 | Gertner |
| 2008/0319435 A1 | 12/2008 | Rioux et al. |
| 2009/0054914 A1 | 2/2009 | Lechner |
| 2009/0062825 A1 | 3/2009 | Pool et al. |

(56) References Cited

U.S. PATENT DOCUMENTS

| | | |
|---|---|---|
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0187202 A1 | 7/2009 | Ortiz et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0220176 A1 | 9/2009 | Fusco |
| 2009/0222031 A1 | 9/2009 | Axelsson |
| 2009/0222065 A1 | 9/2009 | Dlugos, Jr. et al. |
| 2009/0228063 A1 | 9/2009 | Dlugos, Jr. et al. |
| 2009/0228072 A1 | 9/2009 | Coe et al. |
| 2009/0270904 A1 | 10/2009 | Birk et al. |
| 2009/0306462 A1 | 12/2009 | Lechner |
| 2010/0010291 A1 | 1/2010 | Birk et al. |
| 2010/0049224 A1 | 2/2010 | Vargas |
| 2010/0087843 A1 | 4/2010 | Bertolote et al. |
| 2010/0099945 A1 | 4/2010 | Birk et al. |
| 2010/0100079 A1 | 4/2010 | Berkcan |
| 2010/0145378 A1 | 6/2010 | Gertner |
| 2010/0152532 A1 | 6/2010 | Marcotte |
| 2010/0168508 A1 | 7/2010 | Gertner |
| 2010/0185049 A1 | 7/2010 | Birk et al. |
| 2010/0191265 A1* | 7/2010 | Lau et al. .................. 606/157 |
| 2010/0191271 A1 | 7/2010 | Lau et al. |
| 2010/0204647 A1 | 8/2010 | Gertner |
| 2010/0204723 A1 | 8/2010 | Gertner |
| 2010/0217071 A1 | 8/2010 | Ricol |
| 2010/0226988 A1 | 9/2010 | Lebreton |
| 2010/0228080 A1 | 9/2010 | Tavori et al. |
| 2010/0234682 A1 | 9/2010 | Gertner |
| 2010/0249803 A1 | 9/2010 | Griffiths |
| 2010/0280310 A1 | 11/2010 | Raven |
| 2010/0305397 A1 | 12/2010 | Birk et al. |
| 2010/0312046 A1 | 12/2010 | Lau et al. |
| 2010/0312147 A1 | 12/2010 | Gertner |
| 2010/0324358 A1 | 12/2010 | Birk et al. |
| 2010/0324359 A1 | 12/2010 | Birk |
| 2011/0201874 A1 | 8/2011 | Birk et al. |

FOREIGN PATENT DOCUMENTS

| | | |
|---|---|---|
| CN | 1367670 | 9/2002 |
| DE | 4225524 | 2/1994 |
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 | 9/2000 |
| EP | 1072282 | 1/2001 |
| EP | 1105073 | 6/2001 |
| EP | 1396242 | 3/2004 |
| EP | 1396243 | 3/2004 |
| EP | 1491167 | 12/2004 |
| EP | 1491168 | 12/2004 |
| EP | 1529502 | 5/2005 |
| EP | 1547549 | 6/2005 |
| EP | 1574189 | 9/2005 |
| EP | 1600183 | 11/2005 |
| EP | 1602346 | 12/2005 |
| EP | 1704833 | 9/2006 |
| EP | 1719480 | 11/2006 |
| EP | 1736123 | 12/2006 |
| EP | 1736195 | 12/2006 |
| EP | 1736202 | 12/2006 |
| EP | 1743605 | 1/2007 |
| EP | 1829504 | 9/2007 |
| EP | 1829505 | 9/2007 |
| EP | 1829506 | 9/2007 |
| EP | 1967168 | 9/2008 |
| EP | 1992315 | 11/2008 |
| EP | 2074970 | 7/2009 |
| EP | 2074971 | 7/2009 |
| EP | 2074972 | 7/2009 |
| EP | 2095796 | 9/2009 |
| EP | 2095798 | 9/2009 |
| EP | 2191796 | 6/2010 |
| FR | 1566202 | 5/1969 |
| FR | 2688693 | 9/1993 |
| FR | 2769491 | 4/1999 |
| FR | 2783153 | 3/2000 |
| FR | 2797181 | 2/2001 |
| FR | 2799118 | 4/2001 |
| FR | 2823663 | 10/2002 |
| FR | 2855744 | 12/2004 |
| FR | 2921822 | 4/2009 |
| GB | 1174814 | 12/1969 |
| GB | 2090747 | 7/1982 |
| JP | 57-171676 | 10/1982 |
| JP | 1-67309 | 4/1989 |
| JP | 2-019147 | 1/1990 |
| JP | 2-132104 | 11/1990 |
| JP | 3-105702 | 11/1991 |
| JP | 11-244395 | 9/1999 |
| JP | 2003-526410 | 9/2003 |
| JP | 2005-131380 | 5/2005 |
| JP | 2005-334658 | 12/2005 |
| SE | 8503144 | 12/1986 |
| WO | WO 86/00079 | 1/1986 |
| WO | WO 86/00912 | 2/1986 |
| WO | WO 89/11701 | 11/1989 |
| WO | WO 90/00369 | 1/1990 |
| WO | WO 92/20349 | 11/1992 |
| WO | WO 94/02517 | 2/1994 |
| WO | WO 96/33751 | 1/1996 |
| WO | WO 98/35639 | 8/1998 |
| WO | WO 98/35640 | 8/1998 |
| WO | WO 00/00108 | 1/2000 |
| WO | WO 00/01428 | 1/2000 |
| WO | WO 00/09047 | 2/2000 |
| WO | WO 00/09049 | 2/2000 |
| WO | WO 00/15158 | 3/2000 |
| WO | WO 00/66196 | 11/2000 |
| WO | WO 01/10359 | 2/2001 |
| WO | WO 01/12078 | 2/2001 |
| WO | WO 01/41671 | 6/2001 |
| WO | WO 01/47435 | 7/2001 |
| WO | WO 01/47575 | 7/2001 |
| WO | WO 01/49245 | 7/2001 |
| WO | WO 01/52777 | 7/2001 |
| WO | WO 01/68007 | 9/2001 |
| WO | WO 01/85071 | 11/2001 |
| WO | WO 02/05753 | 1/2002 |
| WO | WO 02/09792 | 2/2002 |
| WO | WO 02/19953 | 3/2002 |
| WO | WO 02/26317 | 4/2002 |
| WO | WO 02/053093 | 7/2002 |
| WO | WO 02/065948 | 8/2002 |
| WO | WO 02/096326 | 12/2002 |
| WO | WO 03/007782 | 1/2003 |
| WO | WO 03/055420 | 7/2003 |
| WO | WO 03/057092 | 7/2003 |
| WO | WO 03/059215 | 7/2003 |
| WO | WO 03/077191 | 9/2003 |
| WO | WO 03/101352 | 12/2003 |

(56) References Cited

FOREIGN PATENT DOCUMENTS

| | | |
|---|---|---|
| WO | WO 03/105732 | 12/2003 |
| WO | WO 2004/014245 | 2/2004 |
| WO | WO 2004/019671 | 3/2004 |
| WO | WO 2004/108025 | 12/2004 |
| WO | WO 2004/112563 | 12/2004 |
| WO | WO 2005/007232 | 1/2005 |
| WO | WO 2005/009305 | 2/2005 |
| WO | WO 2005/067994 | 5/2005 |
| WO | WO 2005/072195 | 8/2005 |
| WO | WO 2005/087147 | 9/2005 |
| WO | WO 2005/094447 | 10/2005 |
| WO | WO 2005/112888 | 12/2005 |
| WO | WO 2006/040647 | 4/2006 |
| WO | WO 2006/049725 | 5/2006 |
| WO | WO 2006/083885 | 8/2006 |
| WO | WO 2006/108203 | 10/2006 |
| WO | WO 2007/067206 | 6/2007 |
| WO | WO 2007/081304 | 7/2007 |
| WO | WO 2007/106727 | 9/2007 |
| WO | WO 2007/114905 | 10/2007 |
| WO | WO 2007/145638 | 12/2007 |
| WO | WO 2008/063673 | 5/2008 |
| WO | WO 2008/134755 | 11/2008 |
| WO | WO 2009/050709 | 4/2009 |
| WO | WO 2009/132127 | 10/2009 |
| WO | WO 2009/136126 | 11/2009 |
| WO | WO 2010/042493 | 4/2010 |

OTHER PUBLICATIONS

Acuna-Goycolea et al.; "Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus"; The Journal of Neuroscience; V. 25(32); pp. 7406-7419; Aug. 10, 2005.
Adrian et al.; "Mechanism of Pancreatic Polypeptide Release in Man." The Lancet; pp. 161-163; Jan. 22, 1977.
Anson; "Shape Memory Alloys—Medical Applications," Source: Materials World, vol. 7, No. 12, pp. 745-747, Dec. 1999.
Asakawa et al; "Antagonism of Ghrelin Receptor Reduces Food Intake and Body Weight Gain in Mice"; Gut.; V.52; pp. 947-952; 2003.
Baggio et al. "Biology of Incretins: GLP-1 and GIP"; Gastroenrology; V. 132; pp. 2131-2157; 2007.
Ballantyne; "Peptide YY(1-36) and Peptide YY(3-36): Part I. Distribution, Release, and Actions"; Obesity Surgery; V.16; pp. 651-658; 2006.
Ballantyne; "Peptide YY(1-36) and Peptide YY(3-36): Part II. Changes after Gastrointestinal Surgery and Bariatric Surgery"; Obesity Surgery; V.16; pp. 795-803; 2006.
Berne et al; "Physiology"; V. 5; pp. 55-57, 210, 428, 540, 554, 579, 584, 591; 2004.
BioEnterics Lap-Band Adjustable Gastric Banding System, Inamed Health, pub., pp. 1-115; Aug. 28, 2003.
Boulant et al.; "Cholecystokinin in Transient Lower Oesophageal Sphincter Relaxation Due to Gastric Distension in Humans"; Gut.; V. 40; pp. 575-581; 1997.
Bradjewin et al.; "Dose Ranging Study of the Effects of Cholecystokinin in Healthy Volunteers"; J. Psychiatr. Neurosci.; V. 16 (2); pp. 91-95; 1991.
Brown et al; "Symmetrical Pouch Dilation After Laparoscopic Adjustable Gastric Banding: Incidence and Management"; Obesity Surgery; V. 18, pp. 1104-1108; 2008.
Burdyga et al.; "Cholecystokinin Regulates Expression of Y2 Receptors in Vagal Afferent Neurons Serving the Stomach"; The Journal of Neuroscience; V. 28; No. 45; pp. 11583-11592; Nov. 5, 2008.
Ceelen et al.; "Surgical Treatment of Severe Obesity With a Low-Pressure Adjustable Gastric Band: Experimental Data and Clinical Results in 625 Patients"; Annals of Surgery; V. 237, No. 1; pp. 10-16; 2003.

Chaptini et al.; "Neuroendocrine Regulation of Food Intake"; Current Opinion in Gastroenterology; V. 24; pp. 223-229; 2008.
Chaudhri; "Can Gut Hormones Control Appetite and Prevent Obesity?" Diabetes Care; V. 31; Supp 2; pp. S284-S289; Feb. 2008.
Cohen et al.; "Oxyntomodulin Suppresses Appetite and Reduces Food Intake in Humans"; J. Clin. Endocrinol. Metab.; V. 88; No. 10; pp. 4696-4701; 2003.
Corno et al.; "A new implantable device for telemetric control of pulmonary blood flow"; New ideas; received Apr. 24, 2004; received in revised form Jul. 12, 2002; 10 pages.
Corno et al.; "FlowWatchTM in clipped and inclipped position"; Interact Cardio Vase Thorac Surg 2002; 1:46-49; Copyright @ 2002 The European Association for Cardio-thoracic Surgery; 1 page.
Cummings et al.; "Plasma Ghrelin Levels After Diet-Induced Weight Loss or Gastric Bypass Surgery"; N. Engl J. Med; V. 346, No. 21; pp. 1623-1630; May 23, 2002.
Cummings; "Gastrointestinal Regulation of Foot Intake"; The Food Journal of Clinical Investigation; V. 117, N. 1; pp. 13-23; Jan. 2007.
Dakin et al.; "Oxyntomodulin Inhibits Food Intake in the Rat"; Endocrinology; V. 142; No. 10; pp. 4244-4250; 2001.
Dakin et al.; "Peripheral Oxyntomodulin Reduces Food Intake and Body Weight gain in Rats"; Endocrinology; V. 145; No. 6; pp. 2687-2695; Jun. 2004.
Davison; "Activation of Vagal-Gastric Mechanoreceptors by Cholecystokinin"; Proc. West. Pharmocol. Soc.; V. 29; pp. 363-366; 1986.
De Waele et al.; "Endoscopic Volume Adjustment of Intragastric Balloons for Intolerance"; Obesity Surgery; V. 11; pp. 223-224; 2001.
De Waele et al.; "Intragastric Balloons for Preoperative Weight Reduction"; Obesity Surgery; V. 58; pp. 58-60; 2001.
Desai et al.; "Molecular Weight of Heparin Using 13C Nuclear Magnetic Resonance Spectroscopy" Journal of Pharmaceutical Science, V. 84, I 2; 1995, Abstract only.
Dixon et al.; "Pregnancy After Lap-Band Surgery: Management of the Band to Achieve Healthy Weight Outcomes"; Obesity Surgery; V. 11, pp. 59-65; 2001.
Doldi et al.; "Intragastric Balloon: Another Option for Treatment of Obesity and Morbid Obesity"; Hepato-Gastroenterology; V. 51, N. 55; pp. 294-307; Jan.-Feb. 2004.
Doldi et al.; "Treatment of Morbid Obesity with Intragastric Balloon in Association with Diet"; Obesity Surgery; V. 10, pp. 583-587; 2000.
Doldi et al; "Intragastric Balloon in Obese Patients"; Obesity Surgery; V. 10, 578-581; 2000.
Ekblad et al.; "Distribution of Pancreatic Peptide and Peptide-YY"; Peptides; V. 23; pp. 251-261; 2002.
El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.
Galloro et al; "Preliminary Endoscopic Technical Report of an New Silicone Intragastric Balloon in the Treatment of Morbid Obesity"; Obesity Surgery; V. 9, pp. 68-71; 1999.
GinShiCel MH Hydroxy Propyl Methyl Cellulose, Web Page http://www.ginshicel.cn/MHPC.html, Nov. 12, 2008.
Girard; "The incretins: From the concept to their use in the treatment of type 2 diabetes. Part A: Incretins: Concept and physiological functions"; Diabetes and Metabolism; V. 34; pp. 550-559; 2008.
Greenough et al; "Untangling the Effects of Hunger, Anxiety, and Nausea on Energy Intake During Intravenous Cholecystokinin Octapeptide (CCK-8) Infusion"; Physiology & Behavior; V. 65, No. 2; pp. 303-310; 1998.
Grise et al.; "Peptide YY Inhibits Growth of Human Breast Cancer in Vitro and in Vivo"; Journal of Surgical Research; V. 82; pp. 151-155; 1999.
Grundy; "Signaling the State of the Digestive Tract"; Autonomic Neuroscience: Basic and Clinical; V. 125; pp. 76-80; 2006.
Grundy; "Vagal Control of Gastrointestinal Function"; Bailliere's Clinical Gastroenterology; V. 2; No. 1; pp. 23-43; 1988.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

(56) References Cited

OTHER PUBLICATIONS

Hameed et al.; "Gut hormones and appetite control." Oral Diseases; V. 15; pp. 18-26; 2009.
Hassan et al.; "Effects of Adjuvants to Local Anesthetics on Their Duration III Experimental Studies of Hyaluronic Acid" Abstract Pub Med [Acta Anesthesiol Scand.; 29 (4): 384-8], 1 page; May 1985.
Helioscopie Product Insert for Heliogast, 1 page; Jun. 2009.
Hodson et al.; "Management of Obesity with the New Intragastric Balloon"; Obesity Surgery; V. 11, pp. 327-329, 2001.
Holzer; "Gastrointestinal Afferents as Targets of Novel Drugs for the Treatment of Functional Bowel Disorders and Visceral Pain"; European Journal of Pharmacology; V. 429; pp. 177-193; 2001.
Houpt; "Gastrointestinal Factors in Hunger and Satiety." Neuroscience and Behavioral Reviews; V. 6; pp. 145-164; 1982.
Jones; "Molecular, pharmacological, and clinical aspects of liraglutide, a oncedaily human GLP-1 analogue"; Molecular and Cellular Endocrinology; V. 297; pp. 137-140; 2009.
Kerem et al.; "Exogenous Ghrelin Enhances Endocrine and Exocrine Regeneration in Pancreatectomized Rats"; J Gastrointest Surg.; V. 13; pp. 775-783, 2009.
Kesty et al.; "Hormone-based therapies in the regulation of fuel metabolism and body weight"; Expert Opin. Biol. Ther.; V. 8; No. 11; pp. 1733-1747; 2008.
Kissileff et al.; "Peptides that Regulate Food Intake: Cholecystokinin and Stomach Distension Combine to Reduce Food Intake in Humans"; Am. J. Physiol. Regul. Integr. Comp. Physiol; V. 285; pp. 992-998; 2003.
Kojima et al.; "A role for pancreatic polypeptide in feeding and body weight regulation." Peptides; V. 28; pp. 459-463; 2007.
Kulicke et al. "Visco-Elastic Propeerties of Sodium Hyaluronate Solutions," American Institute of Physics; pp. 585-587; 2008.
Lap-Band AP System Adjustable Gastric Banding System With OmniformTM Design: Directions for Use (DFU); Allergan, 16 pages; 2009.
Le Roux et al.; "Gut Hormone Profiles Following Bariatric Surgery Favor an Anorectic State, Facilitate Weight Loss, and Improve Metabolic Parameters"; Ann. Surg; V. 243; No. 1; pp. 108-114; Jan. 2006.
Liu et al.; "Adjuvant Hormonal Treatment With Peptide YY or Its Analog Decreases Human Pancreatic Carcinoma Growth"; The American Journal of Surgery; V. 171; pp. 192-196; Jan. 1996.
Mathus-Vliegen et al. "Intragastric Balloons for Morbid Obesity: Results, Patient Tolerance and Balloon Life Span"; Br. J. Surg.; V. 77, No. 7, pp. 76-79; Jan. 1990.
Mathus-Vliegen et al. "Treating Morbid and Supermorbid Obesity" International Journal of Gastroenterology; V. 5, No. 1, pp. 9-12; 2000.
Medeiros et al.; "Processing and metabolism of Peptide-YY: Pivotal roles of Dipeptidase-IV, Aminopeptidase-P, and Endopeptidase-24. 11"; Endocrinology; V. 134, No. 5; pp. 2088-2094; 1994.
Naslund et al. "Pranidal subcutaneous injections of glucagon-like peptide-1 cause weight loss in obese human subjects"; British Journal of Nutrition; V. 91; pp. 439-446; 2004.
Neary et al.; "Peptide YY(3-36) and Glucagon-Like Peptide-$1_{(7-36)}$ Inhibit Food Intake Additively"; Endocrinology; V.146; pp. 5120-5127; 2005.
Padidela et al.; "Elevated basal and post-feed glucagon-like petide 1 (GLP-1) concentrations in the neonatel period"; European Journal of Endocrinology; v. 160; pp. 53-58; 2009.
Potier et al.; "Protein, amino acids, and the control of food intake"; Current Opinion in Clinical Nutrition and Metabolic Care; V. 12; pp. 54-58; 2009.
Qjan et al.; "Pulmonary delivery of a GLP-1 receptor agonist, BMS-686117"; International Journal of Pharmaceutics; V. 366; pp. 218-220; 2008.
Rang et al.; "Pharmacology"; V. 5; pp. 203, 397, 402, 524; 2004.
Raybould et al.; "Integration of Postprandial Gastrointestinal Tract: Role of CCK and Sensory Pathways"; Annals of New York Academy of Science; pp. 143-156; 1994.
Renshaw et al. "Peptide YY: A Potential Therapy for Obesity"; Current Drug Targets; V. 6; pp. 171-179; 2005.
Sannino et al.; "Crosslinking of Cellulose Derivatives and Hyaluronic Acid with Water-Soluble Carbodiimide" Polymer 46; pp. 11206-11212; 2005.
Shechter et al.; "Reversible PEGylation of peptide YY3-36 prolongs its inhibition of food intake in mice"; FEBS Letters; V. 579; pp. 2439-2444; 2005.
Shi et al.; "Sexually Dimorphic Responses to Fat Loss After Caloric Restriction or Surgical Lipectomy"; Am. J. Physiol. Endocrinol. Metab.; V. 293; E316-E326; 2007.
Silver et al.; "Physical Properties of Hyaluronic Acid and Hydroxypropylmethylcellulose in Solution: Evaluation of Coating Abillity" Journal of Applied Biomaterials, V. 5; pp. 89-98, 1994.
Small et al.; "Gut hormones and the control of appetite"; TRENDS in Endocrinology and Metabolism; V. 15. No. 6; pp. 259-263; Aug. 2004.
Stanley et al.; "Gastrointestinal Satiety Signals III. Glucagon-like Peptide 1, oxyntomodulin, peptide YY, and pancreatic polypeptide"; Am. J. Physiol Gastrointest Liver Physiol; V. 286; pp. 693-697; 2004.
Tezel; "The Science of Hyaluronic Acid Dermal Fillers," Journal of Cosmetic and Laser Therapy (2008) 10: pp. 35-42.
Tolhurst et al.; "Nutritional regulation of glucagon-like peptide1 secretion"; J. Physiol.; V. 587, No. 1; pp. 27-32; 2009.
Totte et al.; "Weight Reduction by Means of Intragastric Device: Experience with the Bioenterics Intragastric Balloon"; Obesity Surgery; V. 11, pp. 519-523; 2001.
Tough et al.; "$Y_4$ Receptors Mediate the Inhibitory Responses of Pancreatic Polypeptide in Human and Mouse Colon Mucosa"; The Journal of Pharmacology and Experimental Therapeutics; V. 319, No. 1; pp. 20-30; 2006.
Tseng et al; "Peptide YY and cancer: Current findings and potential clinical applications"; Peptides; V. 23; pp. 389-395; 2002.
Valassi et al.; "Neuroendocrine control of food intake"; Nut. Metab. & Cariovasc. Disease; V. 18; pp. 158-168; 2008.
Van Der Lely et al.; "Biological, Physiological, Pathophysiological Aspects of Ghrelin"; Endocrine Reviews; V. 25, No. 3; pp. 426-457; 2004.
Verdich et al. "A Meta-Analysis of the Effect of Glucagon-Like-Peptide-1 (7-36) Amide on ad Libitum Energy Intake in Humans"; J. Clin. Endocrinol. Metab. V. 86; pp. 4382-4389; Sep. 2001.
Wahlen et al.; "The BioEnterics Intragastric Balloon (BIB): How to Use It"; Obesity Surgery; V. 11; pp. 524-527; 2001.
Wang et al.; "Plasma Ghrelin Modulation in Gastric Band Operation and Sleeve Gastrectomy"; Obes. Surg.; pp. 357-362; 2008.
Weiner et al.; "Preparation of Extremely Obese Patients for Laparoscopic Gastric Banding by Gastric Balloon Therapy"; Obesity Surgery; V. 9, pp. 261-264, 1999.
Wynne et al.; "Subcutaneous Oxyntomodulin Reduces Body Weight in Overweight and Obese Subjects: A Double-Blind Randomized, Controlled Trial"; Diabetes; V. 54; pp. 2390-2395; 2005.
Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.
Yuzuriha et al.; "Gastrointestinal Hormones (anorexigenic peptide YY and orexigenic ghrelin) influence neural tube development"; FASEB J.; V. 21; pp. 2108-2112; 2007.

* cited by examiner

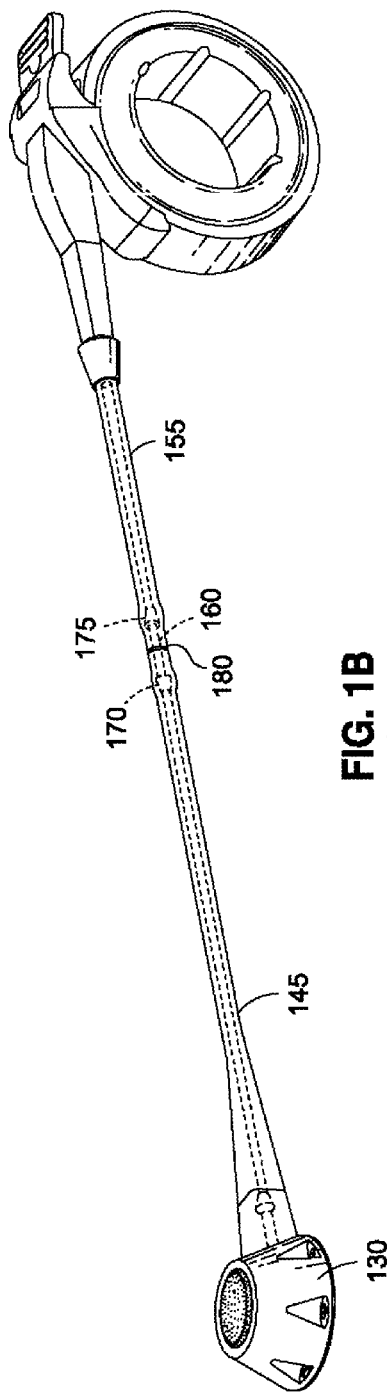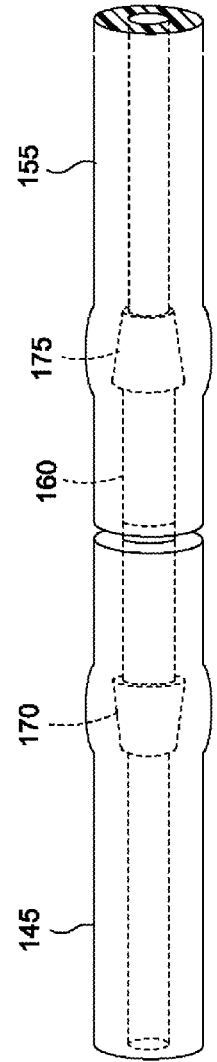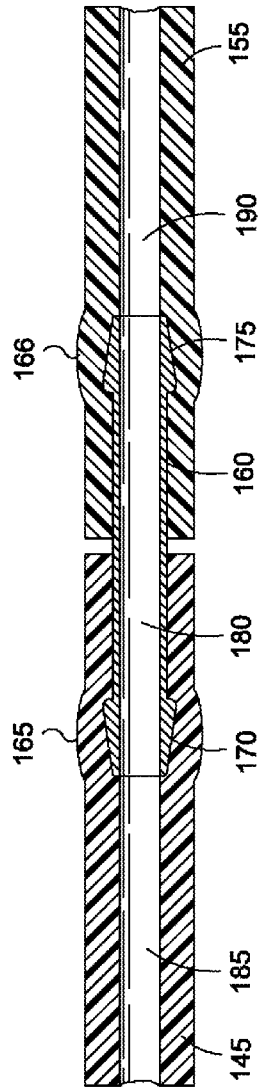
FIG. 1B PRIOR ART
FIG. 1C PRIOR ART
FIG. 1D PRIOR ART

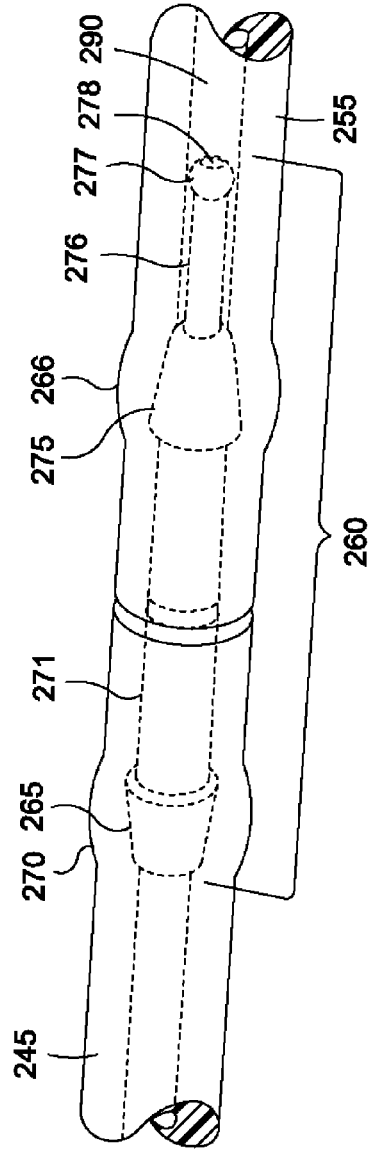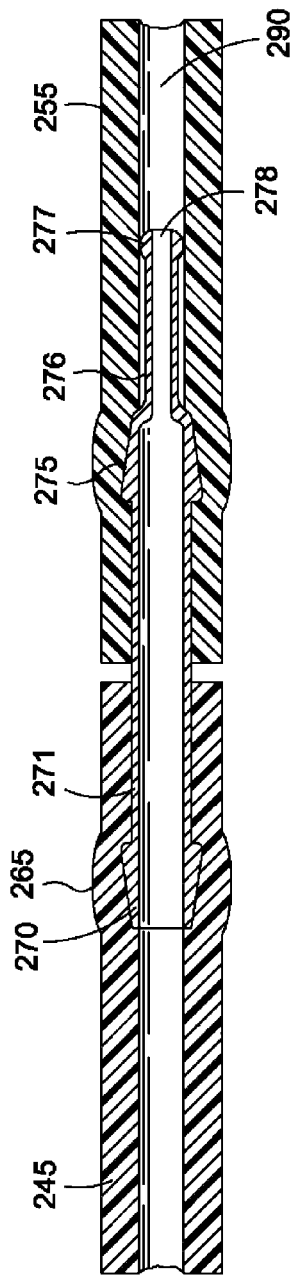

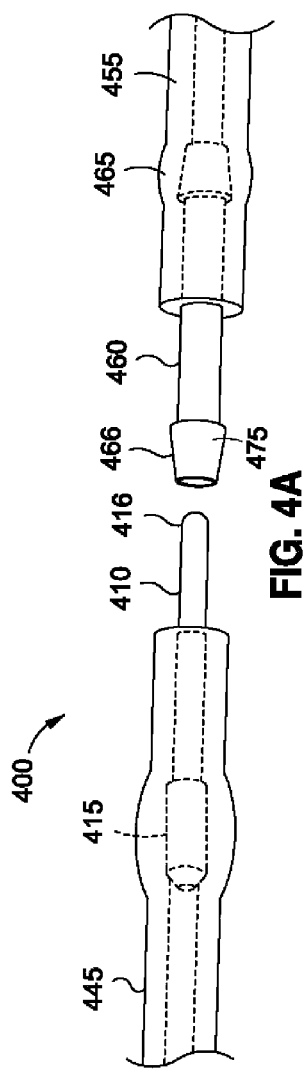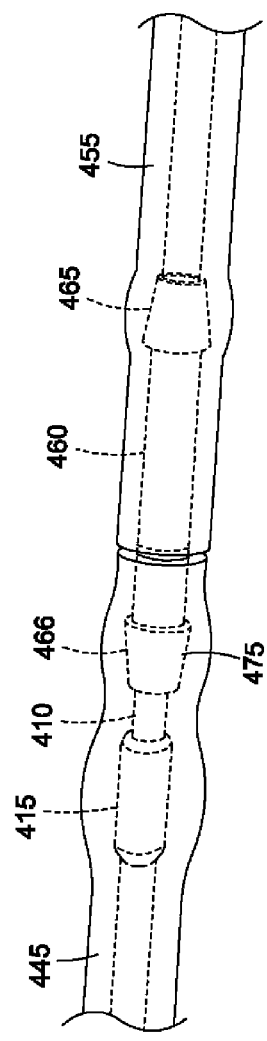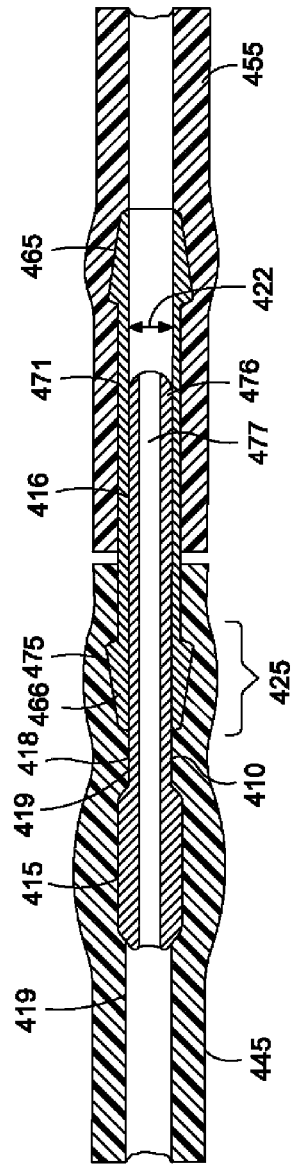

TUBE CONNECTOR WITH A GUIDING TIP

FIELD

The present invention generally relates to medical systems, devices and uses thereof for treating obesity and/or obesity-related diseases. More specifically, the present invention relates to implementing a guiding tip to facilitate the connecting of tubes.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND APO (Allergan, Inc., Irvine, Calif.) gastric band. Generally, gastric bands are placed about the cardia, or upper portion, of a patient's stomach forming a stoma that restricts the food's passage into a lower portion of the stomach. When the stoma is of an appropriate size that is restricted by a gastric band, food held in the upper portion of the stomach may provide a feeling of satiety or fullness that discourages overeating. Unlike gastric bypass procedures, gastric band apparatus are reversible and require no permanent modification to the gastrointestinal tract.

One example of a gastric banding system 105 is illustrated in FIG. 1A. As shown, a body of a patient 100 having a stomach 120 is illustrated. The gastric banding system 105 may be positioned within the patient, forming a constriction about an upper portion of the stomach 120 via a gastric band 110, and more particularly, via an inflatable portion 115 of the gastric band 110. The gastric band 110 may be connected to an access port 130 by means of a connection tube 125. A hypodermic needle 140 may penetrate the skin of the patient 100 and puncture a septum 135 of the access port 130 to add fluid to or remove fluid from the gastric band 110.

Another example of a gastric banding system is disclosed in Roslin, et al., U.S. Patent Pub. No. 2006/0235448, the entire disclosure of which is incorporated herein by this specific reference.

Over time, a stoma created by a gastric band may need adjustment in order to maintain an appropriate size, which is neither too restrictive nor too passive. Accordingly, prior art gastric band systems provide a subcutaneous fluid access port ("access port") connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

Typically, the different components of the gastric banding system, e.g., the access port and the inflatable portion of the gastric band, are coupled or connected to each other via tubing or other fluid conduits. In some instances, it may be practical or desirable to join two pieces of flexible tubing instead of using one long piece of tubing. As shown in FIG. 1B, the access port 130 coupled to a first tube 145 may need to be connected to a second tube 155 in order to establish a fluid path between the access port 130 and the inflatable portion 115 of the gastric band 110.

However, as the gastric banding system 105 is implanted inside a human body, leak prevention is important to reduce or eliminate the need to perform additional surgeries to fix the leaks. Currently, a tube connector 160 having barbed portions 170 and 175 for sealing purposes is being used to connect the two tubes 145 and 155, as shown in FIG. 1B. More particularly, the barbed portions 170 and 175 are utilized to provide a pressure seal and prevent leakage at the location 180 where the two tubes 145 and 155 are joined.

FIG. 1C illustrates a close up view of the tube connector 160 deployed within an inner diameter of the tubes 145 and 155. The barbed portions 170 and 175 of the tube connector 160 may prevent and/or reduce leakage by pressing against the inner diameter of the tubes 145 and 155. As such, necessarily, the barbed portions 170 and 175 have an exterior diameter that is larger than the inner diameter of the tubes 145 and 155.

FIG. 1D illustrates a cross sectional view of FIG. 1C, and more clearly shows the barbed portions 170 and 175 are larger than the inner diameters of the tubes 145 and 155, thereby causing a bulge at locations 165 and 166. Further shown is how the tube connector 160 defines a conduit 180 for coupling conduit 185 to conduit 190. Conduits 180, 185 and 190 may be utilized to carry fluid and/or other substances (e.g., air, gel, etc.) to or removing fluid and/or other substances from the inflatable portion to control the effective size of the gastric band 110.

However, the drawback to having the barb portion larger than the inner diameter of the tube is that it makes it very difficult for the barb portion to be pressed into the tube. FIG. 1E illustrates the barb portion of the tube connector just prior to insertion into the tube.

Furthermore, as with any implantation into the human body, sterility is of the utmost importance and physicians using gloves or other sterility-promoting products may have an even more difficult time when attempting to insert the barbed portion into the tube. FIG. 1F illustrates a cross sectional view of FIG. 1E. Indeed, it may take the physician much time and effort to perform said insertion of the tube connector 160 into the flexible tube 155 considering that the physician has to align the tube connector with the mating end of tube 155, while applying a significant force to cause the initial tube deformation and start the inserting process. In some situations where the tubes may be wet or slippery or very flexible, the inserting process to manipulate the tube connector into the flexible tube may be extremely frustrating.

What is needed is a system that provides the sealing capabilities of the barbed portion while providing improved ease of connecting the tubes.

SUMMARY

Generally described herein are apparatus, systems and methods related to utilizing a guiding tip to connect two open ends of respective tubes of a gastric banding system. More particularly, one of these tubes may include a barbed element at or near the point of connection which makes it difficult to connect the two tubes as the barbed element may be larger than an opening to receive the barbed element. The guiding tip provides a solution to this problem by acting as an interface between the barbed element and the receiving tube. In this manner, the sealing functionality of the barbed element may be retained while improving the ease of inserting the barbed element into the receiving tube.

In one embodiment, provided is a gastric banding system for the treatment of obesity comprising a gastric band having an inflatable portion, an access port having a septum for removing or inserting fluid into the inflatable portion of the gastric band, the access port further having an access port connector. The gastric banding system may also comprise a first tube including a first end connected to the inflatable portion of the gastric band and a second end, the first tube having a first inner diameter, a second tube including a first end connected to the access port connector of the access port and a second end connected to the second end of the first tube, the second tube having a second inner diameter, and a tube connector for connecting the second end of the first tube and the second end of the second tube, the tube connector for fluidly coupling the first tube and the second tube. The tube connector may further include a first barb portion located at a first end of the tube connector, having a diameter larger than the first inner diameter of the first tube, the first barb configured to be pressed into the first inner diameter of the first tube in a factory or other convenient environment using assembly tools and without the typical hindrances of a surgery room, a stem portion located adjacent to the first barb portion, a second barb portion located adjacent to the stem portion, the second barb portion having a diameter larger than the second inner diameter of the second tube, the second barb configured to be pressed into the second inner diameter of second tube, and a guiding tip portion located at a second end of the tube connector, and having an outer diameter not larger than the first inner diameter of the first tube configured to be inserted into the first inner diameter of the first tube.

In one embodiment, provided is a tube connector for connecting a first tube and a second tube comprising a first barb and having a diameter larger than the first inner diameter of the first tube, the first barb configured to be pressed into the first inner diameter of the first tube, a stem portion located adjacent to the first barb, a second barb portion located adjacent to the stem portion, the second barb portion having a diameter larger than the second inner diameter of the second tube, the second barb configured to be pressed into the second inner diameter of second tube, a guiding stem portion adjacent to the second barb, and a guiding tip portion adjacent to the guiding stem portion having an outer diameter not larger than a first inner diameter of the first tube configured to be inserted into the first inner diameter of the first tube.

In one embodiment, provided is a gastric banding system for the treatment of obesity comprising a gastric band having an inflatable portion, an access port having a septum for removing or inserting fluid into the inflatable portion of the gastric band, the access port further having an access port connector, a first tube including a first end connected to the inflatable portion of the gastric band and a second end, the first tube having a first inner diameter, a second tube including a first end connected to the access port connector of the access port and a second end connected to the second end of the first tube, the second tube having a second inner diameter, a female tube connector for connecting the second end of the first tube and the second end of the second tube, and a male connector configured to be inserted into the female connector for connecting the second end of the first tube and the second end of the second tube. The female tube connector may further include a first barb portion located at a first end of the female tube connector, having a diameter larger than the first inner diameter of the first tube, the first barb configured to be pressed into the first inner diameter of the first tube, a stem portion located adjacent to the first barb portion, and a second barb portion located adjacent to the stem portion, the second barb portion having a diameter larger than the second inner diameter of the second tube, the second barb portion configured to be pressed into the second inner diameter of second tube. The male tube may further include an enlarged stem portion located at a first end of the male tube connector, having a diameter larger than the first inner diameter of the second tube, a non-exposed stem portion adjacent to the enlarged stem portion located within the second tube, and an exposed stem portion adjacent to the enlarged stem portion located outside the second tube, the exposed stem portion configured to be inserted into the female connector to establish a fluid connection between the first tube and the second tube.

BRIEF DESCRIPTION OF THE DRAWINGS

The features, obstacles, and advantages of the present invention will become more apparent from the detailed description set forth below when taken in conjunction with the drawings, wherein:

PRIOR ART

PRIOR ART FIG. 1B illustrates the gastric banding system of FIG. 1A having a tube connector.

PRIOR ART FIG. 1C illustrates a close up view of the tube connector of FIG. 1B.

PRIOR ART FIG. 1D illustrates a cross-sectional view of the tube connector of FIG. 1B.

PRIOR ART

PRIOR ART

FIG. 2C illustrates a close up view of the tube connector of FIG. 2A having the guiding tip portion and the barbed portion inserted into a tube according to an embodiment of the present invention.

FIG. 2D illustrates a cross sectional view of FIG. 2C according to an embodiment of the present invention.

FIG. 4A illustrates a tube connection system according to an embodiment of the present invention.

FIG. 4B illustrates a tube connection system of FIG. 4A according to an embodiment of the present invention.

FIG. 4C illustrates a cross sectional view of the tube connection system of FIG. 4A according to an embodiment of the present invention.

DETAILED DESCRIPTION

Apparatuses, systems and/or methods that implement the embodiments of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between referenced elements.

Figure 2A:
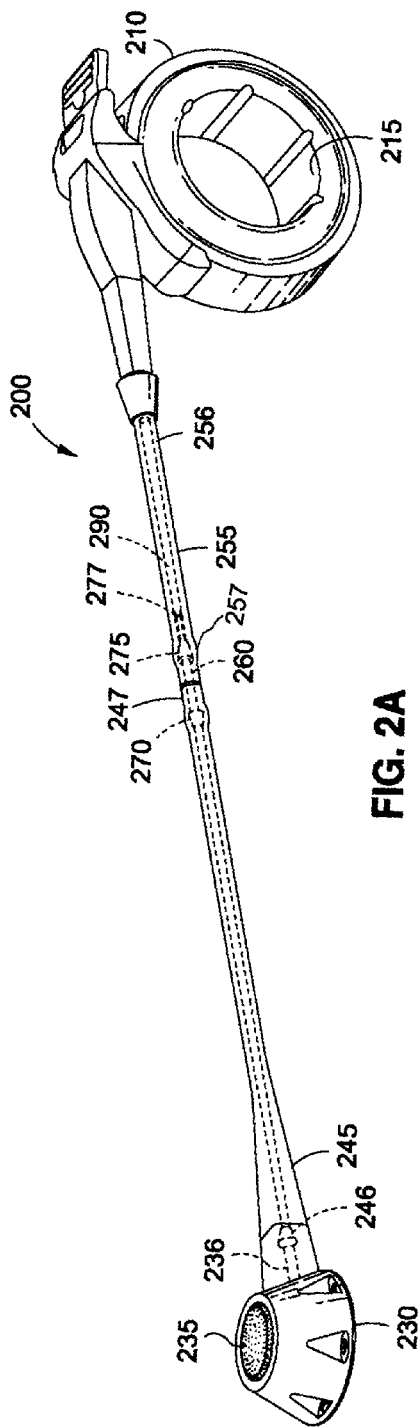
FIG. 2A illustrates the gastric banding system having a tube connector according to an embodiment of the present invention.

Turning to FIG. 2A, illustrated is a gastric banding system 200 include a tube connector 260 having a guiding tip portion 277. The tube connector 260 may be made out of a biocompatible plastic or metal in the shape shown in FIG. 2A. The gastric banding system 200 may include an access port 230 with a septum 235. The access port 230 may include an access port connector 236 for interfacing with a first tube 245. The first tube 245 may be connected to the second tube 255 which may be connected to an inflatable portion 215 of a gastric band 210.

More particularly, the first tube 245 may include a first end 246 and a second end 247. Similarly, the second tube 255 may include a first end 256 and a second end 257. The first end 246 of the first tube 245 may be connected to the access port connector 236 and the second end 247 of the first tube 245 may be connected to the second end 257 of the second tube 255. The first end 256 of the second tube 255 may be connected to the inflatable portion 215 of the gastric band 210. In this manner, a pathway may be established between the access port 230 and the gastric band 210.

Figure 2B:
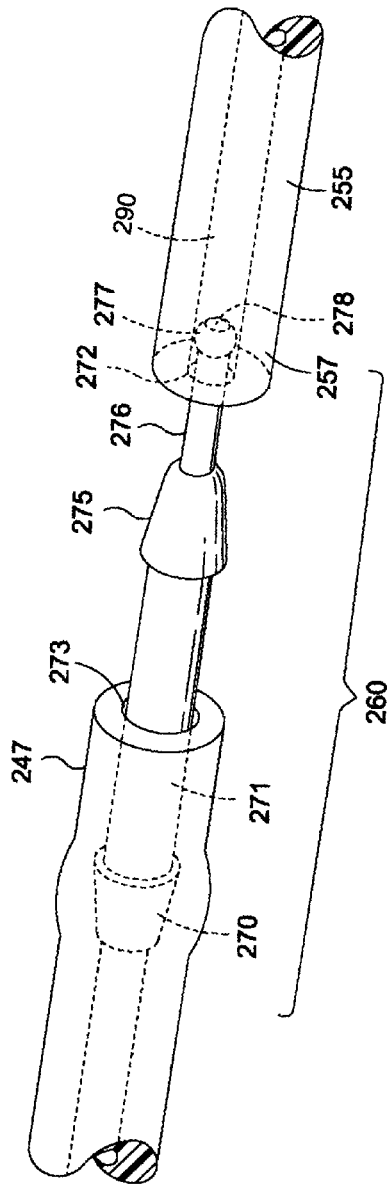
FIG. 2B illustrates a close up view of the tube connector of FIG. 2A having only guiding tip portion inserted into a tube according to an embodiment of the present invention.

FIGS. 2B and 2C illustrate close-up views of how the guiding tip 277 improves the ease of attaching the second end 247 of the first tube 245 to the second end 257 of the second tube 255. As shown, extending from the second barb portion 275 is a guiding stem portion 276 culminating in a rounded, ball-shaped guiding tip portion 277. The guiding tip portion 277 may be designed to be rounded in order to ensure that the guiding tip portion 277 does not stab or damage the inner diameter of the second tube 255 when inserted. Notably, the outer diameter of the guiding tip portion 277 is no larger than the inner diameter of the second tube 255, thereby making it much easier for the physician to insert the guiding tip portion 277 into the inner diameter of the second tube 255. Once inserted, the physician can apply a force to press the second barb portion 275 into the inner diameter of the second tube 255 without having to align the second barb portion 275 with the opening 272 of the second tube 255 as the guiding tip portion 277 and the guiding stem portion 276 is already inserted and functions to align the second barb portion 275 with the opening 272. Furthermore, as the physician is applying the force, the physician does not have to worry that the second barb portion 275 will slip away from position because by virtue of already being inserted the guiding tip portion 277, in a sense, holds the second barb portion 275 from slipping away from the correct inserting position. As a result, the guiding tip portion 277 and the guiding stem portion 276 allows the physician to press the second barb portion 275 into the inner diameter of the second tube 255 in a much more efficient manner. FIG. 2C illustrates the second barb portion 275 as inserted into the second tube 255 creating the bulge 266 thereby providing a fluid seal at the location of the bulge 266.

FIG. 2D illustrates a cross sectional view of FIG. 2B and better illustrates the differences in diameter sizes of the various components. In this embodiment, the outer diameter of the guiding stem portion 276 may have the smallest diameter. Next, the guiding tip portion 277 may have a diameter larger than or equal to the guiding stem portion 276. The guiding stem portion 276 and the guiding tip portion 277 are configured to be smaller than the inner diameter 290 of the second tube 255 so that a physician may easily insert these portions into the second tube 255. The second barbed portion 275 and/or the stem portion 271 may be larger than the inner diameter 290 of the second tube 255 to prevent leaking of fluid out of the connection location between the first tube 245 and the second tube 255.

Figure 2E:
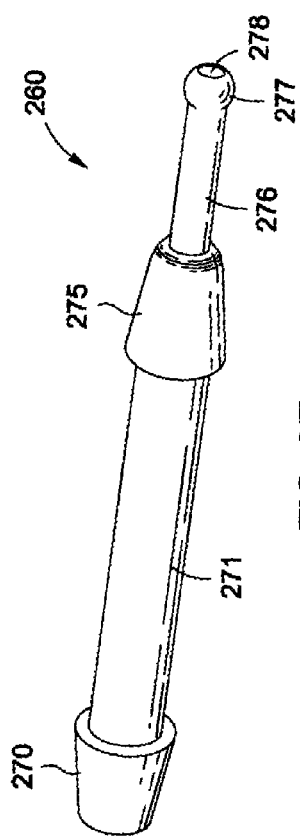
FIG. 2E illustrates the tube connector of FIG. 2A apart from the tube according to an embodiment of the present invention.

The functionality and the inter-relationships of the different components having been described, attention will now be turned to the connector 260 itself. FIG. 2E illustrates the tube connector 260 apart from the tubes 245 and 255. In this embodiment, the connector 260 appears similar to connector 160, except with the connector 260 further includes the features of the guiding stem portion 276 and the guiding tip portion 277. The ball-shaped guiding tip portion 277, in addition to advantageously being shaped to avoid scraping the inner wall of the second tube 255 during insertion, may also be configured to be slightly larger than the guiding stem portion 276 in order to serve as a visual aid to the physician during the initial insertion process.

Figure 2F:
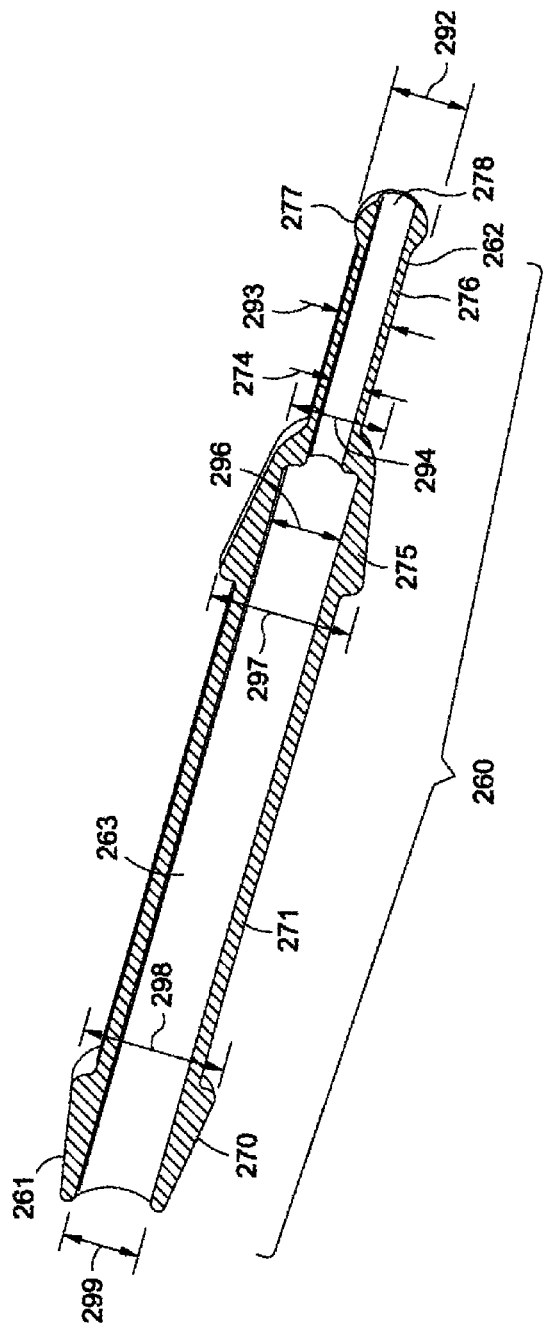
FIG. 2F illustrates a cross sectional view of the tube connector of FIG. 2A apart from the tube according to an embodiment of the present invention.

FIG. 2F illustrates a cross sectional view revealing an inner cavity 263 extending from a first end 261 of the connector 260 to a second end 262 of the connector 260. As shown, the inner cavity 263 may be utilized to pass fluid or other substances from the first end 261 to the second end 262 and vice versa. When the connector 260 is inserted into a first tube and a second tube, the inner cavity 263 may be utilized to pass fluid between the first tube and the second tube. As illustrated, the connector 260 has a varying topology. Proximal to the first end 261, the first barb 270 may define a first outer diameter 299 and a second outer diameter 298. The first barb 270 gradually increases in diameter between the first outer diameter 299 and the second outer diameter 298, while maintaining a constant sized inner cavity 263 (as marked by 296). The stem portion 271 also shares the constant sized inner cavity 263 while having an outer diameter smaller than the second outer diameter 298. The stem portion 271 leads to the second barb 275 which includes a first outer diameter 297 sized to be greater than a second outer diameter 294, gradually decreasing in diameter moving away from the stem portion 271. However, at the second outer diameter 294, an inner diameter 276 of the inner cavity 263 is reduced between the second outer diameter 294 and the guiding tip portion 276. At this same portion, the outer diameter 274 of the guiding stem portion 276 is decreased as compared to the second outer diameter 294 and before increasing at the outer diameter 292 of the guiding tip portion 277. Advantageously, the reduced inner diameter 276 of the inner cavity 263 allows for a minimum wall thickness while still providing sufficient rigidity. In other words, the outer diameter 292 of the guiding tip portion 277 and the outer diameter 247 of the guiding stem portion 276 are small enough to fit through the opening of a tube, while the wall defining the inner diameter 276 is still thick enough to provide sufficient rigidity to structurally support the guiding tip portion 277 and the guiding stem portion 276 of the connector 260.

The above descriptions corresponding to FIG. 2A-2F describe certain embodiments of a connector. However, many other embodiments are also possible. For example, a second guiding stem portion and a second guiding top portion may be integrated or attached to the connector 260 proximal to the first end 261 to achieve similar functionality at the first end 261 of the connector 260.

Figure 3A:
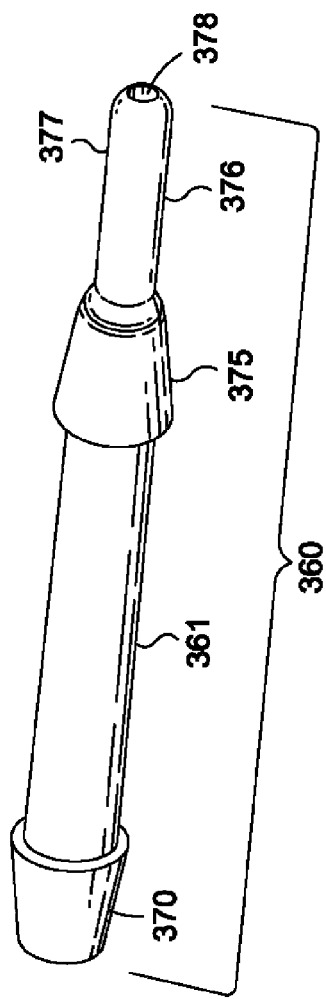
FIG. 3A illustrates a tube connector of the tube according to an embodiment of the present invention.

FIG. 3A illustrates another embodiment of a connector 360 having a first barb portion 370 and a second barb portion 375 with a stem portion 361 therein between. Attached to the second barb portion 375 is a guiding stem portion 376, which culminates in a guiding tip portion 377 defining an opening 378. The functionality of the connector 360 is generally similar to the functionality of the connector 260. However, as compared to the connector 260, the connector 360 of FIG. 3A does not include the ball feature at the guiding tip portion 377, and instead may include a thicker wall to increase rigidity. The embodiment of FIG. 3A may be advantageous in situations where a larger load is desirably carried by the connector 360.

Figure 3B:
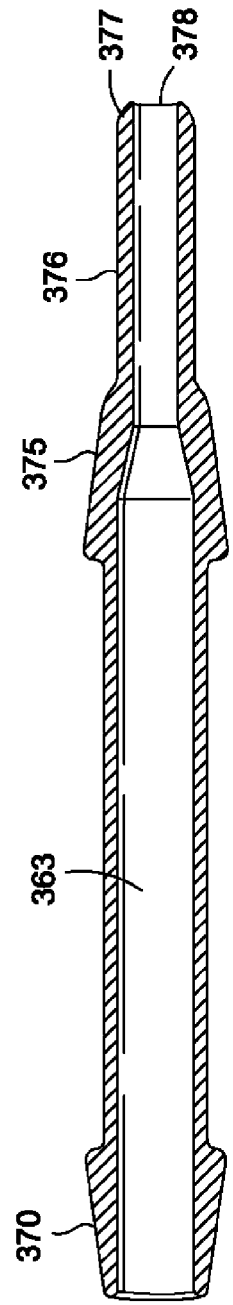
FIG. 3B illustrates a cross sectional view of the tube connector of FIG. 3A according to an embodiment of the present invention.

FIG. 3B illustrates a cross sectional view of the connector 360 of FIG. 3A. The connector 360 may include a tapered inner diameter of cavity 363 at the location of second barb portion 375 to reduce turbulence and promote smooth fluid flow with less resistance.

Generally, the connectors 260, 360 of FIGS. 2A and 3A, respectively, may involve connecting two flexible tubes where one end of the connector may be pre-inserted into one of the flexible tubes. This situation may be typical of operations or surgeries where only one tube needs to be cut to a customized length at the time of the surgery and therefore, pre-inserting a fitting into the tube to be cut would not be useful since it has to be cut. However, in certain scenarios, there might not be a need to customize the length at the time of the surgery (e.g., in the field) and therefore, a dual-connector system may make the field assembly easier.

Figure 1A:
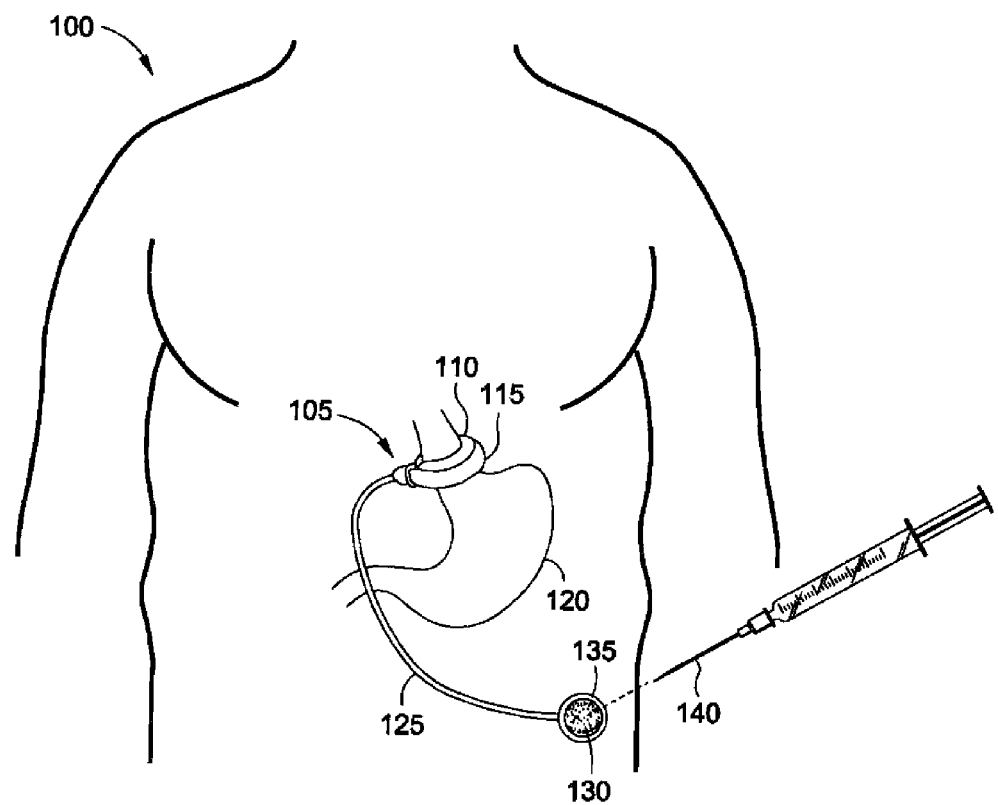
FIG. 1A illustrates a gastric banding system implanted within a patient's body.
Figure 1E:
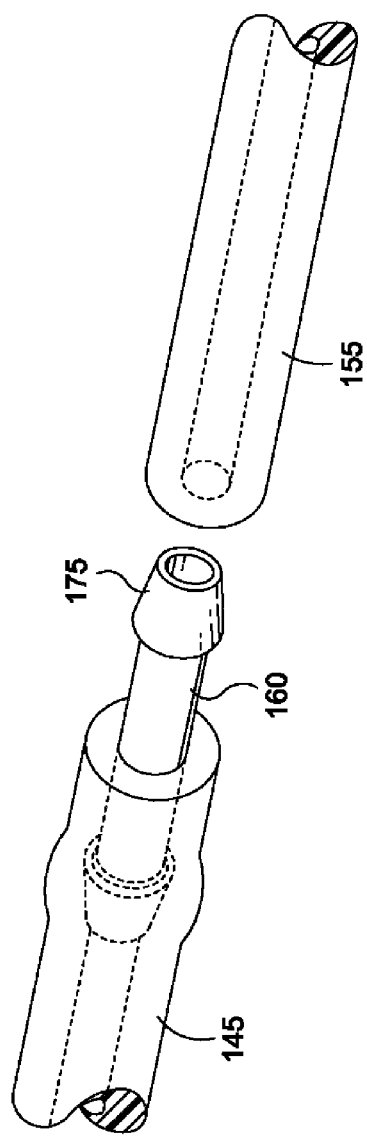
FIG. 1E illustrates a perspective view of a portion of the tube connector of FIG. 1B prior to insertion into the tube.
Figure 1F:
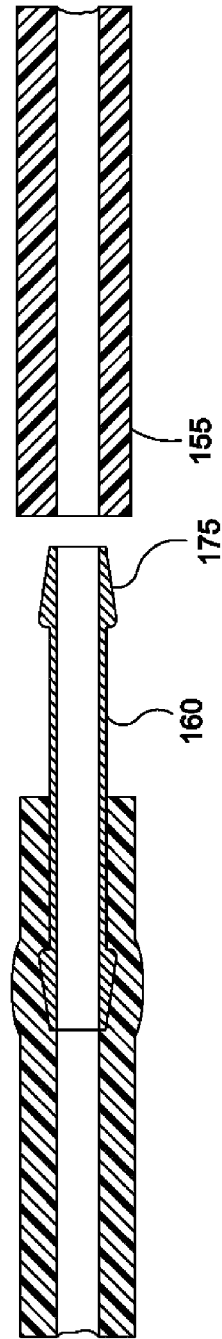
FIG. 1F illustrates a cross sectional view of a portion of the tube connector of FIG. 1E prior to insertion into the tube.

Turning to FIG. 4A, a tubing connecting system 400 is illustrated. The tubing connecting system 400 may include a first connector 410 having a first end 415 pre-attached or inserted in a first tubing 445 and exposing a second end 416. The tubing system 400 may also include a second connector 460 having a first end 465 pre-attached or inserted in a second tubing 455 and exposing a second end 466. In one embodiment, the second connector 460 may be very similar to the connector 160 as illustrated in FIG. 1E. One significant difference between the tubing connecting system 400 and the prior art system illustrated in FIG. 1A-1F is the inclusion of the first connector 410. The first connector 410 serves as a guiding rod for locating and aligning with the opening at the second end 466 of the second connector 460. In this manner, the two tubes 445 and 455 may be connected by inserting the second end 416 of the first connector 410 into the second end 466 of the second connector 460 and pressing the two tubes 445 and 455 together. FIG. 4B illustrates how the tubing connecting system 400 may appear when the second end 416 of the first connector 410 is inserted into the second end 466 of the second connector 460 and the two tubes 445 and 455 are pressed together. In this manner, by designing the second end 416 of the first connector 410 to easily fit within the second end 466 of the second connector 460, the physician is not required to spend much time and/or effort to perform joining the two tubes 445 and 455.

FIG. 4C illustrates a cross sectional view of the tube connector system 400 of FIG. 4B showing how the first connector 410 (e.g., a male connector) is inserted and held in place by a second connector 471 (e.g., a female connector), thereby connecting and holding the two tubes 445 and 455 in place. The outer diameter 477 of the first connector 410 proximal to the guiding stem portion 476 may be the same or smaller than the inner diameter 472 of the second connector 471 to facilitate an easy insertion process. As the guiding stem portion 476 is inserted, the second end 466 (e.g., a second barbed portion 475) may penetrate and be positioned between the outer surface 418 of the first connector 410 and the inner surface 419 of the first tube 445. More particularly, the second end 466 of the second connector may squeeze between said inner surface 491 of the first tube 445 and the outer surface 418 of the first connector 410. Advantageously, the fit of the second end 466 within the first tube 445 may be tight to promote good sealing and leak prevention. Furthermore, the second barbed portion 475 at the second end 466 may serve to limit any leaking that may be present.

Figure 4E:
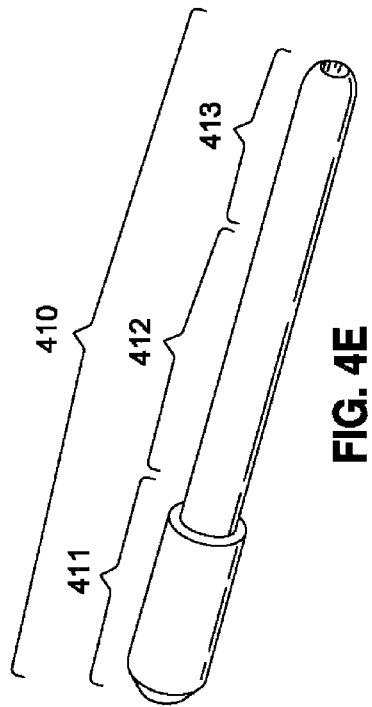
FIG. 4E illustrates a cross sectional view of the tube connector of FIG. 4D disposed within the tube according to an embodiment of the present invention.
Figure 4D:
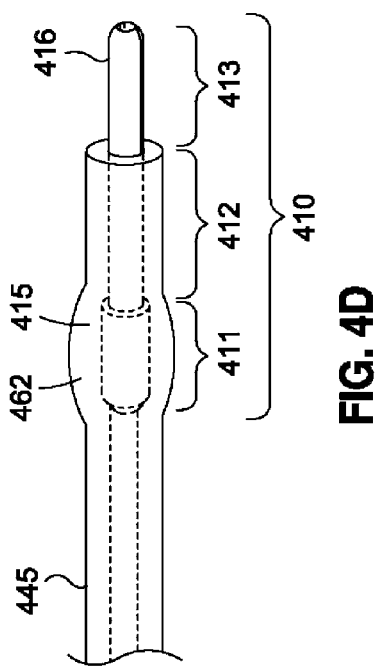
FIG. 4D illustrates the tube connector of FIG. 4A disposed within the tube according to an embodiment of the present invention.

FIGS. 4D and 4E illustrates the first tube 445 and the first connector 410 with the other portions of the connector system 400 omitted for clarity. As shown here, the first connector 410 may include a large stem portion 411 at the first end 462, which may be larger in diameter than the inner diameter of the first tube 445 thereby causing a bulge 462. The large stem portion 411 may be attached to the non-exposed stem portion 412, which is attached to the exposed stem portion 413 located at the second end 416 of the connector 410. The non-exposed stem portion 412 and the exposed stem portion 413 may have a smaller diameter than the diameter of the large stem portion 411. More particularly, in one embodiment, the non-exposed stem portion 412 and the exposed stem portion 413 may have the same or smaller diameter as the inner diameter of the first tube 445. The outer surface of the non-exposed stem portion 412 and the exposed stem portion 413 are not adhered to the inner surface of the first tube 445 so that the second barb portion 475 (shown in FIGS. 4A-4C) may separate and be squeezed in between the outer surface of the non-exposed stem portion 412 and the inner surface of the first tube 445 during the insertion process (as shown in FIG. 4C).

Figure 4F:
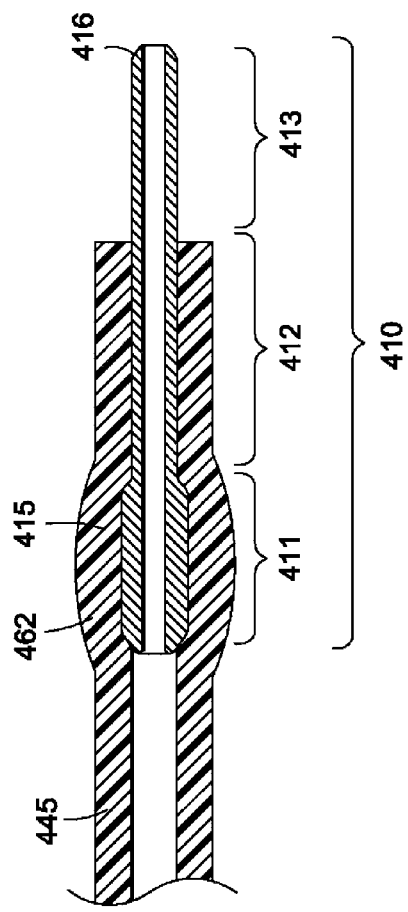
FIG. 4F illustrates a tube connector of the tube according to an embodiment of the present invention.

FIG. 4F illustrates the first connector 410 without the first tube 445 for clarity. As shown here, structurally, the non-exposed stem portion 412 and the exposed stem portion 413 might not be delineated in any manner, and may be defined by which portions are inside the first tube 445 and which portions are outside the first tube 445. However, the large stem portion 411 is shown to have a larger outer diameter than rest of the connector 410.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A gastric banding system for a treatment of obesity, the gastric banding system comprising:
    a gastric band having an inflatable portion;
    an access port having a septum for removing or inserting fluid into the inflatable portion of the gastric band and an access port connector;
    a first tube including a first end connected to the inflatable portion of the gastric band and a second end, the first tube having a first inner diameter;
    a second tube including a first end connected to the access port connector of the access port and a second end connected to the second end of the first tube, the second tube having a second inner diameter; and
    a tube connector for connecting the second end of the first tube and the second end of the second tube, the tube connector for fluidly coupling the first tube and the second tube, the tube connector including:
        a first barb portion located at a first end of the tube connector and having a diameter larger than the first inner diameter of the first tube, the first barb portion configured to be pressed into the first inner diameter of the first tube,
        a stem portion located adjacent to the first barb portion,
        a second barb portion located adjacent to the stem portion, the second barb portion having a diameter larger than the second inner diameter of the second tube, the second barb portion configured to be pressed into the second inner diameter of the second tube, and
        a guiding tip portion located at a second end of the tube connector and having an outer diameter not larger than the first inner diameter of the first tube configured to be inserted into the first inner diameter of the first tube.

2. The gastric banding system of claim 1 further comprising a guiding stem portion adjacent to the guiding tip portion.

3. The gastric banding system of claim 2 wherein the guiding tip portion is ball shaped and has an outer diameter larger than an outer diameter of the guiding stem portion.

4. The gastric banding system of claim 3 wherein the first barb portion and the guiding tip portion may each include an opening at the respective ends of the tube connector for receiving fluid for carrying between the first tube and the second tube.

5. The gastric banding system of claim 4 wherein the first barb portion, the stem portion, the second barb portion, the guiding stem portion and the guiding tip portion combine to define a cavity adapted to carry fluid between the first tube and the second tube.

6. The gastric banding system of claim 5 wherein the cavity has a first diameter proximal to the first barb portion, the stem portion and the second barb portion, and has a second diameter proximal to the guiding stem portion and the guiding tip portion.

7. The gastric banding system of claim 6 wherein the first diameter of the cavity is larger than the second diameter of the cavity.

8. The gastric banding system of claim 7 wherein the tube connector is constructed out of a biocompatible plastic or metal.

9. In a gastric banding system, a tube connector for connecting a first tube and a second tube, the tube connector including:
    a first barb having a diameter larger than a first inner diameter of the first tube, the first barb configured to be pressed into the first inner diameter of the first tube;
    a stem portion located adjacent to the first barb;
    a second barb portion located adjacent to the stem portion, the second barb portion having a diameter larger than a second inner diameter of the second tube, the second barb portion configured to be pressed into the second inner diameter of the second tube;
    a guiding stem portion adjacent to the second barb portion; and a guiding tip portion adjacent to the guiding stem portion having an outer diameter not larger than the first inner diameter of the first tube and configured to be inserted into the first inner diameter of the first tube.

10. The tube connector of claim 9 wherein the guiding tip portion is ball-shaped and has an outer diameter larger than the outer diameter of the guiding stem portion.

11. The tube connector of claim 9 wherein the guiding tip portion is rounded and has a diameter equal to the outer diameter of the guiding stem portion.

12. The tube connector of claim 9 wherein the first barb portion and the guiding tip portion may each include an opening at the respective ends of the tube connector configured to receive fluid for carrying between the first tube and the second tube.

13. The tube connector of claim 12 wherein the first barb portion, the stem portion, the second barb portion, the guiding stem portion and the guiding tip portion combine to define a cavity adapted to carry fluid between the first tube and the second tube.

14. The tube connector of claim 13 wherein the cavity has a first diameter proximal to the first barb portion, the stem portion and the second barb portion, and has a second diameter proximal to the guiding stem portion and the guiding tip portion.

15. The tube connector of claim 14 wherein the first diameter of the cavity is larger than the second diameter of the cavity.

16. A gastric banding system for a treatment of obesity, the gastric banding system comprising:
a gastric band having an inflatable portion;
an access port having a septum for removing or inserting fluid into the inflatable portion of the gastric band, the access port further having an access port connector;
a first tube including a first end connected to the inflatable portion of the gastric band and a second end, the first tube having a first inner diameter;
a second tube including a first end connected to the access port connector of the access port and a second end connected to the second end of the first tube, the second tube having a second inner diameter;
a female tube connector for connecting the second end of the first tube and the second end of the second tube, the female tube connector including:
a first barb portion located at a first end of the female tube connector, having a diameter larger than the first inner diameter of the first tube, the first barb portion configured to be pressed into the first inner diameter of the first tube,
a stem portion located adjacent to the first barb portion, and
a second barb portion located adjacent to the stem portion, the second barb portion having a diameter larger than the second inner diameter of the second tube, the second barb portion configured to be pressed into the second inner diameter of the second tube; and
a male connector configured to be inserted into the female connector for connecting the second end of the first tube and the second end of the second tube, the male tube connector including:
an enlarged stem portion located at a first end of the male tube connector, having a diameter larger than the second inner diameter of the second tube,
a non-exposed stem portion adjacent to the enlarged stem portion located within the second tube, and
an exposed stem portion adjacent to the enlarged stem portion located outside the second tube, the exposed stem portion configured to be inserted into the female connector to establish a fluid connection between the first tube and the second tube.

17. The gastric banding system of claim 16 wherein the second barb portion is further configured to be positioned between the second inner diameter of second tube and an outer surface of the non-exposed stem portion when the second barb portion is inserted into the second tube.

18. The gastric banding system of claim 16 wherein an outer diameter of the exposed stem portion is no larger than an inner diameter of the second barb portion.

19. The gastric banding system of claim 16 wherein the first barb portion, the stem portion, and the second barb portion combine to define a first cavity for receiving the exposed stem portion, and further wherein the exposed stem portion is configured to fit within the first cavity.

20. The gastric banding system of claim 16 wherein the exposed stem portion further defines a second cavity for carrying the fluid between the first tube and the second tube.

* * * * *